(12) United States Patent
Shimizu et al.

(10) Patent No.: US 7,666,611 B2
(45) Date of Patent: Feb. 23, 2010

(54) LYSOPHOSPHATIDIC ACID RECEPTOR

(75) Inventors: Takao Shimizu, Tokyo (JP); Satoshi Ishii, Tokyo (JP); Kyoko Noguchi, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 26 days.

(21) Appl. No.: 10/542,217

(22) PCT Filed: Dec. 17, 2003

(86) PCT No.: PCT/JP03/16176

§ 371 (c)(1), (2), (4) Date: Jul. 15, 2005

(87) PCT Pub. No.: WO2004/063224

PCT Pub. Date: Jul. 29, 2004

(65) Prior Publication Data

US 2006/0264361 A1    Nov. 23, 2006

(30) Foreign Application Priority Data

Jan. 15, 2003    (JP) .............................. 2003-007657

(51) Int. Cl.
*G01N 33/53* (2006.01)
*C12Q 1/00* (2006.01)
(52) U.S. Cl. .............................. 435/7.2; 435/4; 435/7.1
(58) Field of Classification Search ........................ None
See application file for complete search history.

(56) References Cited

FOREIGN PATENT DOCUMENTS

| | | |
|---|---|---|
| EP | 853126 A2 | 7/1998 |
| WO | WO-02/053737 A1 | 7/2002 |
| WO | WO-02/061087 A2 | 8/2002 |
| WO | WO-02/068591 A2 | 9/2002 |

OTHER PUBLICATIONS

Noguchi et al., Identification of p2y9/GPR23 as a novel G protein-coupled receptor for lysophosphatidic acid, structurally distant from the Edg family. J. Biol. Chem. I278:25600-25606, Jul. 11, 2003.*
Brian F. O'Dowd, et al., Cloning and chromosomal mapping of four putative novel human G-protein-coupled receptor genes, Gene, 1997, vol. 187, pp. 75-81 & SwissProt database Accession N. Q99677.
Rodolphe Janssens, et al., Cloning of a Human Heptahelical Receptor Closely Related to the P2Y5 Receptor, Blochem, Biophysics, Res. Comm., 1997, vol. 236, pp. 106-112 & SwissProt database Accession No. Q99677.
International Search Report mailed on Mar. 30, 2004.
International Preliminary Examination Report mailed on Jan. 28, 2005.
English translation of International Preliminary Examination Report for PCT/JP2003/016176 mailed on Jul. 28, 2005.
Noguchi et al., "Identification of P2Y9/GPR23 As a Novel G Protein-Coupled Receptor for Lysophosphatidic Acid, Structurally Distant from the EDG Family", The Journal of Biological Chemistry, vol. 278, No. 28, Jul. 11, 2003, pp. 25600-25606, XP002357510.
Supplementary European Search Report dated Dec. 22, 2005.
European Office Action dated Jan. 15, 2007 for corresponding Application No. 03 780 842.5-2401.

* cited by examiner

*Primary Examiner*—Ruixiang Li
(74) *Attorney, Agent, or Firm*—Westerman, Hattori, Daniels & Adrian, LLP

(57) ABSTRACT

It is intended to provide a novel receptor of LPA and a method of screening a drug such as an LPA receptor antagonist using the same. Use as a lysophosphatidic acid (LPA) receptor comprising a G protein-coupled protein p2y9. More specifically, use of the G protein-coupled protein p2y9 as a lysophosphatidic acid (LPA) receptor. A method of screening an agonist or an antagonist to the LPA receptor as described above by using the receptor.

10 Claims, 29 Drawing Sheets

Fig. 18

```
  1'  MGDRRFIDFQFQDSNSSLRPRLGNATANNTCIVDDSFKYNLNGAVYSVVFILGLITNSVS
           .....*. .*****.* *  ..*.**.***..*.*.
  1"                     MVSVNSSHCFYNDSFKYTLYGCMFSMVFVLGLVSNCVA

61'  LFVFCFRMKMRSETAIFITNLAVSDLLFVCTLPFKIFYNFNRHWPFGDTLCKISGTAFLT
      ...*    .*.*.**.....***.****** ****.***   .*.***** *****   * *
 39"  IYIFICVLKVRNETTTYMINLAMSDLLFVFTLPFRIFYFTTRNWPFGDLLCKISVMLFYT

121'  NIYGSMLFLTCISVDRFLAIVYPFRSRTIRTRRNSAIVCAGVWILVLSGGISASLFSTTN
      *.***.*****************.*.*.**.**.  ***.***.  *..*.  .*  .  .*.
 99"  NMYGSILFLTCISVDRFLAIVYPFKSKTLRTKRNAKIVCTGVWLTVIGGSAPAVFVQSTH

181'  V--NNATTTCFEGFSKRVWKTYLSKITIFIEVVGFIIPLILNVSCSSVVLRTLRKPATLS
         ***...***.*.. .******.*.****.***.******.***.**.** **.***
159"  SQGNNASEACFENFPEATWKTYLSRIVIFIEIVGFFIPLILNVTCSSMVLKTLTKPVTLS

239'  QIGTNKKKVLKMITVHMAVFVVCFVPYNSVLFLYALVRSQAITNCFLERFAKIMYPITLC
      .  .**.****** **. .*  ******   *.**.***.*...**  .   ...*******
219"  RSKINKTKVLKMIFVHLIIFCFCFVPYNINLILYSLVRTQTFVNCSVVAAVRTMYPITLC

299'  LATLNCCFDPFIYYFTLESFQKSFYINAHIRMESLFKTETPLTTKPSLPAIQEEVSDQTT
      .*. ******..**** ...*.*. ...    . * *.
279"  IAVSNCCFDPIVYYFTSDTIQNSIKMKNWSVRRSDFRFSEVHGAENFIQHNLQTLKSKIF

359'  NNGGELMLESTF

339"  DNESAA
```

SEQUENCE LISTING

<160> NUMBER OF SEQ ID NOS: 1

<210> SEQ ID NO 1
<211> LENGTH: 370

-continued

```
<212> TYPE: PRT
<213> ORGANISM: Human

<400> SEQUENCE: 1

Met Gly Asp Arg Arg Phe Ile Asp Phe Gln Phe Gln Asp Ser Asn Ser
 1               5                  10                  15

Ser Leu Arg Pro Arg Leu Gly Asn Ala Thr Ala Asn Asn Thr Cys Ile
             20                  25                  30

Val Asp Asp Ser Phe Lys Tyr Asn Leu Asn Gly Ala Val Tyr Ser Val
         35                  40                  45

Val Phe Ile Leu Gly Leu Ile Thr Asn Ser Val Ser Leu Phe Val Phe
     50                  55                  60

Cys Phe Arg Met Lys Met Arg Ser Glu Thr Ala Ile Phe Ile Thr Asn
 65                  70                  75                  80

Leu Ala Val Ser Asp Leu Leu Phe Val Cys Thr Leu Pro Phe Lys Ile
                 85                  90                  95

Phe Tyr Asn Phe Asn Arg His Trp Pro Phe Gly Asp Thr Leu Cys Lys
            100                 105                 110

Ile Ser Gly Thr Ala Phe Leu Thr Asn Ile Tyr Gly Ser Met Leu Phe
        115                 120                 125

Leu Thr Cys Ile Ser Val Asp Arg Phe Leu Ala Ile Val Tyr Pro Phe
    130                 135                 140

Arg Ser Arg Thr Ile Arg Thr Arg Arg Asn Ser Ala Ile Val Cys Ala
145                 150                 155                 160

Gly Val Trp Ile Leu Val Leu Ser Gly Gly Ile Ser Ala Ser Leu Phe
                165                 170                 175

Ser Thr Thr Asn Val Asn Asn Ala Thr Thr Thr Cys Phe Glu Gly Phe
            180                 185                 190

Ser Lys Arg Val Trp Lys Thr Tyr Leu Ser Lys Ile Thr Ile Phe Ile
        195                 200                 205

Glu Val Val Gly Phe Ile Ile Pro Leu Ile Leu Asn Val Ser Cys Ser
    210                 215                 220

Ser Val Val Leu Arg Thr Leu Arg Lys Pro Ala Thr Leu Ser Gln Ile
225                 230                 235                 240

Gly Thr Asn Lys Lys Lys Val Leu Lys Met Ile Thr Val His Met Ala
                245                 250                 255

Val Phe Val Val Cys Phe Val Pro Tyr Asn Ser Val Leu Phe Leu Tyr
            260                 265                 270

Ala Leu Val Arg Ser Gln Ala Ile Thr Asn Cys Phe Leu Glu Arg Phe
        275                 280                 285

Ala Lys Ile Met Tyr Pro Ile Thr Leu Cys Leu Ala Thr Leu Asn Cys
    290                 295                 300

Cys Phe Asp Pro Phe Ile Tyr Tyr Phe Thr Leu Glu Ser Phe Gln Lys
305                 310                 315                 320

Ser Phe Tyr Ile Asn Ala His Ile Arg Met Glu Ser Leu Phe Lys Thr
                325                 330                 335

Glu Thr Pro Leu Thr Thr Lys Pro Ser Leu Pro Ala Ile Gln Glu Glu
            340                 345                 350

Val Ser Asp Gln Thr Thr Asn Asn Gly Gly Glu Leu Met Leu Glu Ser
        355                 360                 365

Thr Phe
    370
```

US 7,666,611 B2

LYSOPHOSPHATIDIC ACID RECEPTOR

This application is a 371 of International Application No. PCT/JP03/16176 filed on Dec. 17, 2003.

TECHNICAL FIELD

The present invention relates to a novel receptor of lysophosphatidic acid (LPA). More particularly, it relates to a lysophosphatidic acid (LPA) receptor comprising G protein-coupled protein p2y9, use of the G protein-coupled protein p2y9 as a lysophosphatidic acid (LPA) receptor and a method of screening an agonist or an antagonist to the LPA receptor by using the same.

BACKGROUND ART

Lysophosphatidic acid (LPA) is a kind of glycero-phospholipids with a lipid bonded to one of the hydroxyl groups in the glycerin structure. LPA is a substance generated from glycerophospholipid, where one of two lipid moieties has been hydrolyzed through the intervention of phospholipase. As representative examples of LPA, such as 1-acyl-glycerol-3-phosphate, 2-acyl-glycerol-3-phosphate and 1-alkenyl-glycerol-3-phosphate are known.

LPA, present only in trace amounts in vivo, has been recognized merely as intermediate or resolvent occurring during biosynthesis of glycerophospholipid. Recently however, it has been revealed that LPA is a primary component of lipid growth factor present in serum (see Prior Art Reference 22), having a variety of physiological activities, and thus has attracted the public attention as one of physiologically active lipids.

LPA is found to be a substance that stimulates cell proliferation, and is indispensable for recovery of the damaged tissue. It has also been reported that LPA induces retraction of neurite which is essential to the maturation of neuron, and carcinoma cell invasion. Moreover, LPA has come to be known to have a variety of functions in diverse tissues such as smooth muscle contraction, platelet aggregation, suppression of cell apoptosis and promotion of cellular chemotaxis. Further, a number of patent applications relating to "The method of detecting the ovarian cancer by detecting LPA in plasma" (see Prior Art Reference 1), "The method for determining the level of lysophosphate acid such as LPA in a sample" (see Prior Art Reference 2), "The method of producing Lysophosphatidate Phosphatase which specifically hydrolyzes LPA" (see Prior Art Reference 3) and "Cloning of human Lysophosphatidate Phosphatase" (see Prior Art Reference 4) have been filed.

As described above, it has been revealed that LPA is not merely an intermediate or resolvent but itself is a kind of mediator having a variety of physiological activities. Accordingly, LPA, same as a platelet activating factor (PAF) and sphingosine-1-phosphate (S1P), has come to be recognized as one of "lysophospholipid mediators".

It has been recognized that LPA exhibits its physiological activities by binding to G-protein-coupled receptor (GPCR) expressed on the surface of the cell membrane. Namely, the receptor of LPA has been recognized as a seven transmembrane GPCR, however, remained substantially unknown over a long period of time. It is because, LPA being a kind of lysophospholipids and fat-soluble, even the existence of its receptor has been doubted due to the difficulties in carrying out membrane binding assay or in finding a suitable antagonist.

However, in 1996, genes of LPA receptor named vzg-1 (see Prior Art Reference 23) and PSP24 (see Prior Art Reference 24) were cloned. It was named vzg-1 (ventricular zone gene-1). It is because vzg-1, a seven transmembrane GPCR specific to the cell in the neocortical ventricular zone, where interkinetic nuclear movement of neuroblast harmonious to cell progression cycle has been observed during the developmental process of the mouse brain. To date, vzg-1 was identified as a mouse homologue of edg-2 gene, which has been isolated as a sheep-derived orphan receptor, and is now known as edg-2 gene.

In addition to edg-2 (vzg-1), a number of genes exhibiting a high degree of sequence identity such as edg-1, edg-3 and edg-4 have been recorded in EST database, and recognized to form a group of EDG (endothelial cell differentiation gene) family. EDG family divides into two subgroups according to their homology, one is a group of edg-2 and edg-4 which functions as LPA receptor, another is a group of edg-1 and edg-3 which functions as S1P (sphingosine-1-phosphate) receptor.

PSP24 gene exhibits fairly little sequence homology to the above described edg-2 gene, however, the expression of the homologous gene to PSP24 has been observed in mouse nerve system and human fatal brain. Since the gene products thereof also exhibit reactivity with LPA, it is considered to form an independent group. Human PSP24 gene also has been isolated from adult human brain cDNA library (see Prior Art Reference 5) based on the base sequence of PSP24 gene of *Xenopus laevis* oocyte.

EDG family and PSP24 being members of GPCR, the known GPCRs to date are shown in FIG. 1. FIG. 1 is a phylogenetic tree, wherein the location of each protein has been determined based on the homology in amino acid sequence thereof, and those exhibiting a higher degree of sequence homology are placed in the vicinity while those exhibiting lower degree of sequence homology have been placed in a way off. The numbers in FIG. 1 represent measurement for the relative value indicating lower degree of sequence homology between individual proteins. Closed circles (●) in FIG. 1 represent the known receptors for lipids, whereas gray circles represent the receptors known for other than lipids. Generic names of ligands are displayed in outskirt of the tree. EDG family is located in the lower right in FIG. 1. And PSP24 is located close to the lower center. Open circles in FIG. 1 represent the orphan receptors whose ligands have not been identified yet.

p2y9, a GPCR of the present invention, is located in the lower left in FIG. 1. Thus, it is apparent from FIG. 1 that p2y9 shares no homology in amino acids sequences with known EDG family or PSP24.

The novel GPCRs are being identified even now, and disclosed in the published patent applications such as Japanese Unexamined Patent Publication No. 2002-355045 (see Prior Art Reference 6), Japanese Unexamined Patent Publication No. 2002-17378 (see Prior Art Reference 7) and other patent applications (see Prior Art References 8 to 18). The patent applications relating to the method for modifying the function of GPCR (see Prior Art Reference 19), the method for regulating transcription of G2A receptor (see Prior Art Reference 20), and the method for screening the activity of GPCR (see Prior Art Reference 21) have been filed.

Prior art references relating to the present invention are shown below, and those are incorporated herein by reference.
1. Japanese Unexamined Patent Publication No. 2002-328132
2. Japanese Unexamined Patent Publication No. 2002-017398

3. Japanese Unexamined Patent Publication No. 2000-152782
4. Domestic re-publication of PCT international publication WO00/031275
5. Domestic re-publication of PCT international publication WO99/024569
6. Japanese Unexamined Patent Publication No. 2002-355045
7. Japanese Unexamined Patent Publication No. 2002-17378
8. Japanese Unexamined Patent Publication No. 2001-245674
9. Japanese Unexamined Patent Publication No. 2001-245673
10. Japanese Unexamined Patent Publication No. 2001-245672
11. Japanese Unexamined Patent Publication No. 2001-211889
12. Japanese Unexamined Patent Publication No. 2001-190281
13. Japanese Unexamined Patent Publication No. 2001-186888
14. Japanese Unexamined Patent Publication No. 2001-169786
15. Japanese Unexamined Patent Publication No. 2001-161385
16. Japanese Unexamined Patent Publication No. 2001-161383
17. Japanese Unexamined Patent Publication No. 2001-161382
18. Published Japanese translation of a PCT application No. 2002-501083
19. Published Japanese translation of a PCT application No. 2002-523091
20. Published Japanese translation of a PCT application No. 2001-523456
21. Published Japanese translation of a PCT application No. H11-505718/1999
22. van Corven E., et al., Cell, 59, 45-54 (1989)
23. Hecht, J. H., et al., J. Cell. Biol., 135, 1071-1083 (1996)
24. Guo, Z., et al., Proc. Natl. Acad. Sci. USA, 93, 14367-14372 (1996)

DISCLOSURE OF THE INVENTION

Although LPA is one of the lysophospholipid mediators having diverse physiological activities in vivo, the receptor thereof has not yet been well characterized. Therefore, it is important to identify the receptor of LPA for a variety of LPA associated physiological activities as well as treatment and prevention of various diseases. Accordingly, once a novel receptor for LPA becomes available, it will have a variety of applications for the development of pharmaceutical preparations including screening or evaluation of pharmaceutical preparations such as new types of LPA receptor antagonist.

This invention is to provide a novel receptor for LPA and a method for screening pharmaceutical preparations such as antagonist of LPA receptor using the same.

BRIEF DESCRIPTION OF THE DRAWINGS

FIG. 2 shows an example of the expression vector where HA tagged DNA encoding p2y9 was inserted between KpnI and NheI sites in vector pCXN2.1.

FIG. 16 shows the result with no treatment with forskolin (5 μM). The horizontal axis shows the concentration of LPA (nM), whereas the vertical axis shows the ratio of changes in cAMP concentration. The closed square (■) represents clone of p2y9, closed triangle (▲) represents clone of p2y5, closed diamond (◆) represents negative control i.e. a clone transfected with empty vector. The solid line shows the result in the absence of pertussis toxin (PTX), whereas the broken line shows the result in the presence of pertussis toxin (PTX).

FIG. 18 shows the homology in amino acid sequence between p2y9 of the present invention and p2y5. The sequence of p2y9 is displayed on top of the sequence of p2y5 with asterisks (*) indicating the matching amino acid residues.

FIG. 19 represents the result of the negative control. The horizontal axis represents the added tritium labeled LPA (nM), whereas the vertical axis represents the detected radiation (dpm). The diagonally lined bar in the graph represents the total bindings, the white (open) bar on the right represents the nonspecific bindings and the closed triangle (▲) represents the specific bindings.

FIG. 20 represents the result of p2y5. The horizontal axis represents the added tritium labeled LPA (nM), whereas the vertical axis represents the detected radiation (dpm). The diagonally lined bar in the graph represents the total bindings, the white (open) bar on the right represents the nonspecific bindings and the closed triangle (▲) represents the specific bindings.

FIG. 21 represents the result of p2y9 of the present invention. The horizontal axis represents the added tritium labeled LPA (nM), whereas the vertical axis represents the detected radiation (dpm). The diagonally lined bar in the graph represents the total bindings, the white (open) bar on the right represents the nonspecific bindings and the closed triangle (▲) represents the specific bindings.

FIG. 22 represents the result of the negative control. The horizontal axis represents the added tritium labeled LPA (nM), whereas the vertical axis represents the detected radiation (dpm). The diagonally lined bar in the graph represents the total bindings, the white (open) bar on the right represents the nonspecific bindings and the closed triangle (▲) represents the specific bindings.

FIG. 23 represents the result of p2y5. The horizontal axis represents the added tritium labeled LPA (nM), whereas the vertical axis represents the detected radiation (dpm). The diagonally lined bar in the graph represents the total bindings, the white (open) bar on the right represents the nonspecific bindings and the closed triangle (▲) represents the specific bindings.

FIG. 24 represents the result of p2y9 of the present invention. The horizontal axis represents the added tritium labeled LPA (nM), whereas vertical axis represents the detected radiation (dpm). The diagonally lined bar in the graph represents the total bindings, the white (open) bar on the right represents the nonspecific bindings and the closed triangle (▲) represents the specific bindings.

FIG. 26 shows the result of the membrane fractions derived from the cells where p2y9 were introduced. The horizontal axis in FIG. 26 shows the concentration of tritium labeled LPA (nM), whereas the vertical axis shows the detected radiation (dpm). The closed square (■) represents the total bindings, closed diamond (♦) represents the nonspecific bindings and open circle (○) represents the specific bindings.

FIG. 27 represents the negative control. The horizontal axis in FIG. 27 shows the concentration of tritium labeled LPA (nM), whereas the vertical axis shows the detected radiation (dpm). The closed square (■) represents the total bindings, closed diamond (♦) represents the nonspecific bindings and open circle (○) represents the specific bindings.

BEST MODE FOR CARRYING OUT THE INVENTION

The present inventors have conducted the study of orphan receptors (FIG. 1 on the left) which share homology with a platelet activating factor receptor (PAFR) shown in phylogenetic tree constructed based on homology in amino acid sequences of G protein-coupled receptor (GPCR), and unexpectedly found that p2y9, one of orphan receptors sharing homology with a platelet activating factor receptor (PAFR), exhibited stronger reactivity with LPA rather than the platelet activating factor (PAF). Namely, the present inventors have completed the invention by finding a novel and totally different type of LPA receptor from those of known receptors.

The present invention relates to a use as a lysophosphatidic acid (LPA) receptor comprising a G protein-coupled protein p2y9. Particularly, it relates to a use of a G protein-coupled protein p2y9 as a lysophosphatidic acid (LPA) receptor. More particularly, it relate to a use of a G protein-coupled protein p2y9 having amino acid sequence represented by SEQ ID NO:1 as a lysophosphatidic acid (LPA) receptor.

The present invention further relates to a method of screening an agonist or an antagonist to the LPA receptor by using the LPA receptor of the present invention described above.

The present invention is intended to clarify that a G protein-coupled protein p2y9 functions as a lysophosphatidic acid (LPA) receptor. Namely, it is to elucidate that LPA functions as a ligand for a G protein-coupled protein p2y9.

The present inventors have been interested in the orphan receptors which share homology with a platelet activating factor receptor (PAFR) such as GPR34, p2y5, p2y9 (GPR23 for another name) and p2y10, and have conducted a study of ligands thereof. Since each of those receptors sharing homology with a platelet activating factor receptor (PAFR), a platelet activating factor (PAF) or the related substances have been predicted to be ligands thereof. Whereas p2y9 (GPR23 for another name) exhibited no reactivity with a platelet activating factor (PAF) or the related substances, but unexpectedly exhibited higher reactivity with LPA. The present inventors have thus found that p2y9 is a receptor that recognizes LPA as a ligand thereof. The amino acid sequence of p2y9 being scarcely identical to those of EDG-2, EDG-4, EDG-7 and PSP24, which is recognized from the phylogenetic tree of FIG. 1. The present inventors therefore have found a new type of receptor completely different from those of known ones.

The present inventors obtained the clones which stably expressing GPR34, p2y5, p2y9 (GPR23 for another name) and p2y10 by introducing DNAs encoding amino acids sequences of GPR34, p2y5, p2y9 (GPR23 for another name) and p2y10 tagged at N terminus with HA, which is the foreign peptides comprising 9 amino acids residue, independently into the pCXN2.1 vectors; transfecting CHO cells with pCXN2.1 vectors; and thereby selecting clones highly expressing HA-tags on the cell surfaces.

Figure 2:
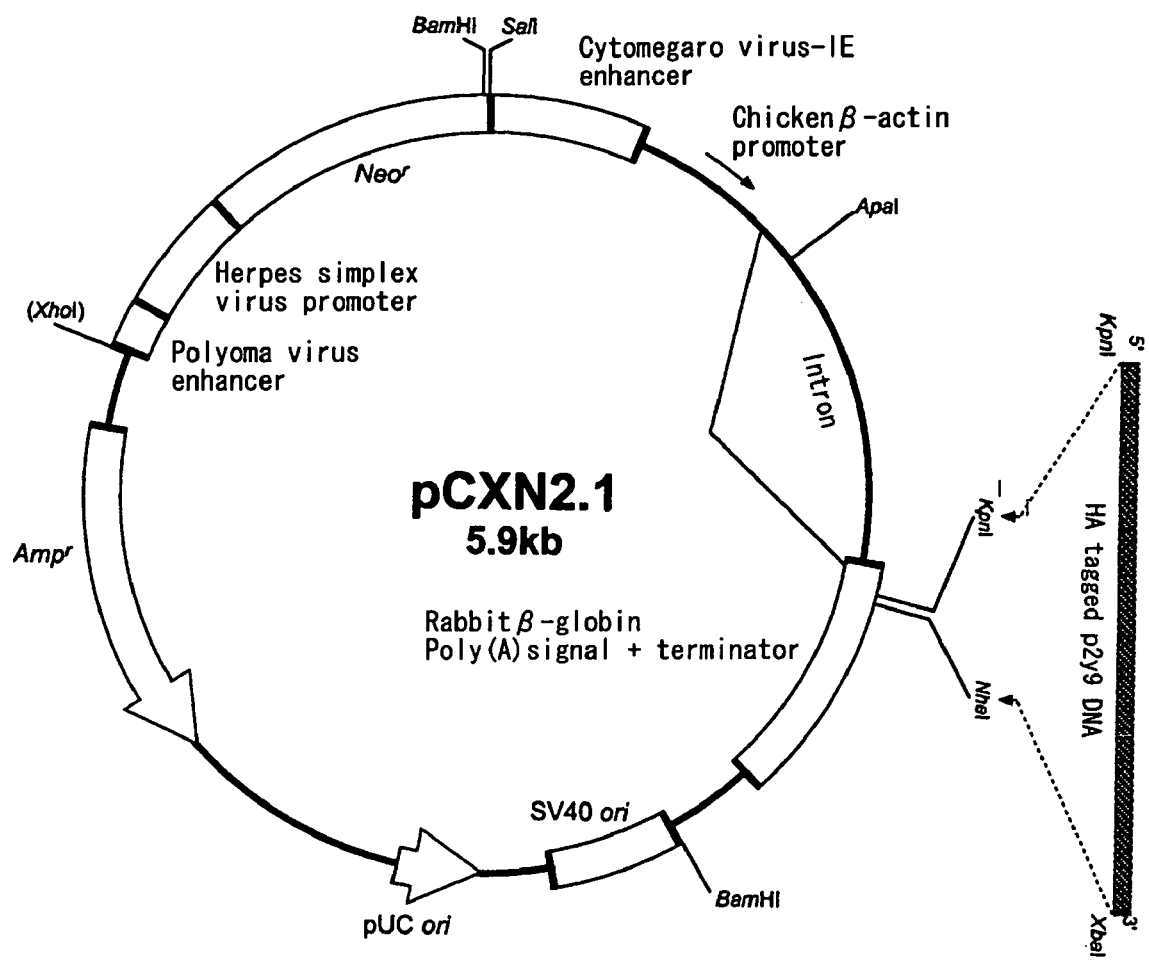
FIG. 2 shows the example of a vector for introducing p2y9 of the present invention into a cell.

FIG. 2 shows the expression vector wherein DNA encoding HA-tagged p2y9 is inserted at a site between KpnI and NheI of pCXN2.1 vector. Vectors were constructed independently for other receptors in the same manner. p2y9 used for a test experiment is a protein comprising 370 amino acids of which amino acid sequence is represented by SEQ ID NO: 1 in the sequence listing.

1-oleoyl-LPA represented by the following formula:

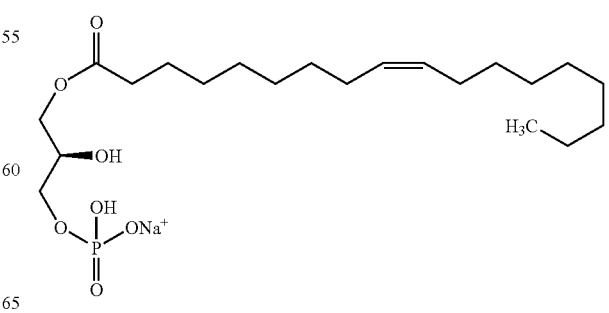

was used as LPA in the above described experiment.

Over 200 lipids (Lipid Library; BIOMOL) and nucleotides were screened using CHO clones of respective receptors by monitoring changes in intracellular calcium concentrations. As positive controls for the screenings, ATP with concentrations of 1 μM, 10 μM and 100 μM were used. Since ATP receptors are endogenously expressed in CHO cells, a significant change in calcium concentration can be observed with addition of ATP. In the positive controls, due to the addition of ATP, the changes in calcium concentration beyond the measurable range have been observed in respective concentrations, proving that the experiment itself was a success.

On the other hand, an increase in intracellular calcium concentration specific to the receptor expressed by transfection was observed when the clone expressing p2y9 was stimulated with LPA. A significant change in calcium concentration in CHO cells transfected with DNA encoding p2y9 was recognized as a result of such screenings.

Figure 3:
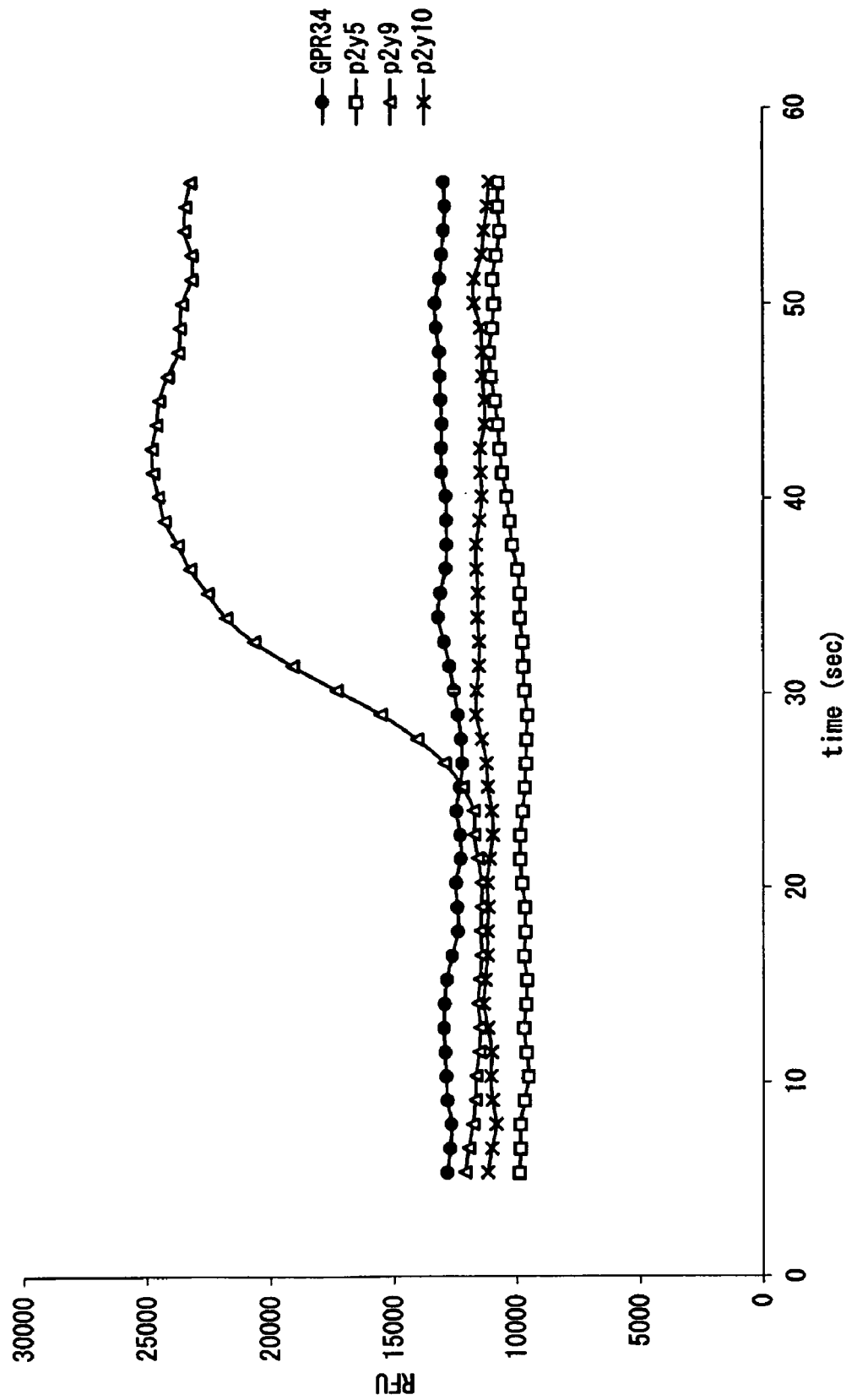
FIG. 3 shows the results of close investigation on changes in calcium concentration in each cell induced by LPA (10 µM) by using CHO clones of respective receptors. The vertical axis in FIG. 3 represents a calcium concentration (RFU), whereas the horizontal axis represents time (sec). Closed circle (●) in FIG. 3 represents GPR 34, open square (□) represents p2y5, open triangle (Δ) represents p2y9 and (x) represents p2y10 respectively.
Figure 4:
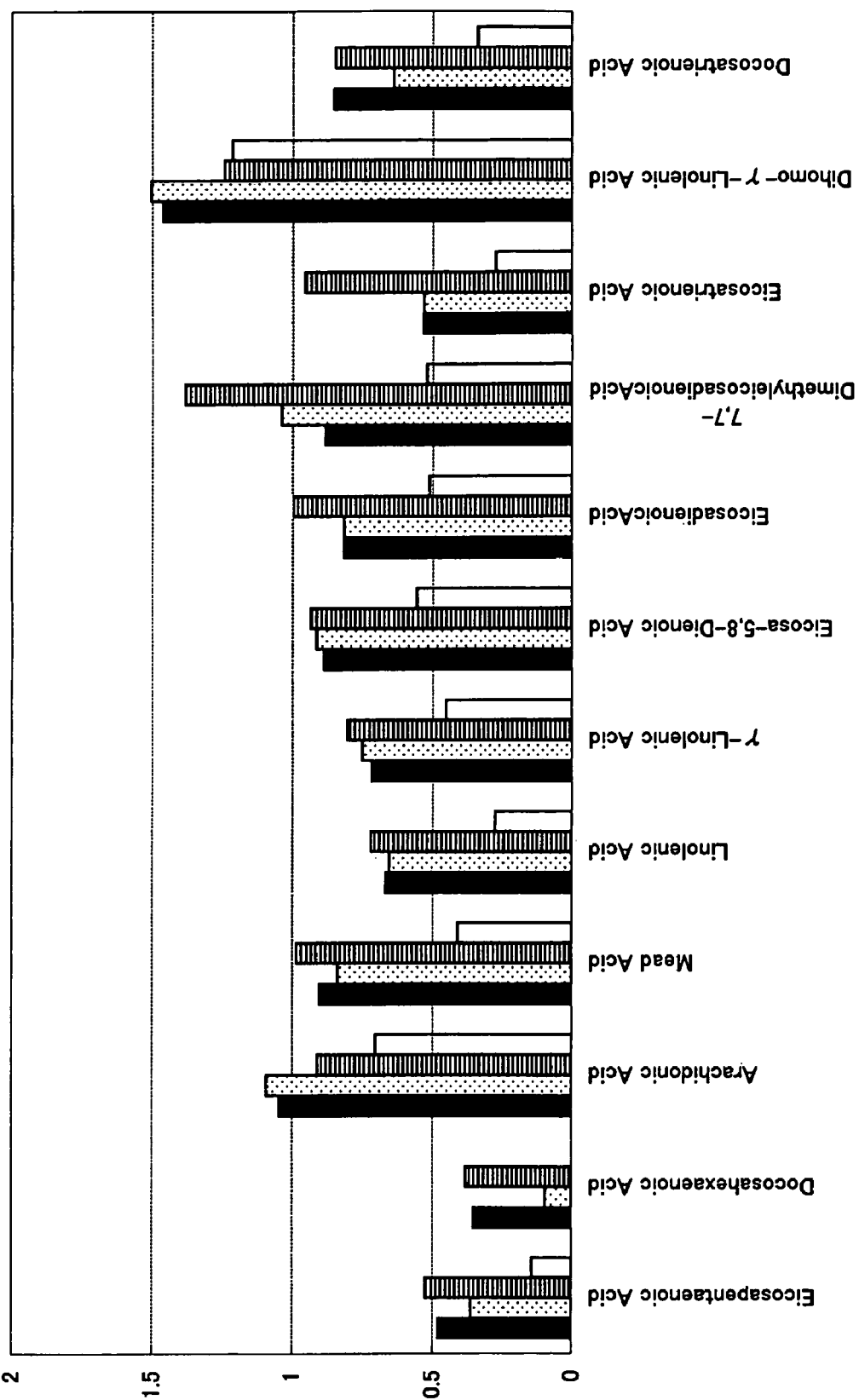
FIG. 4 shows the results of the changes in intracellular cAMP concentration by using CHO clones respectively expressing four types of receptors such as GPR34, p2y5, p2y9 and p2y10 with addition of various kinds of lipids or nucleotides. The added lipids and nucleotides were as shown in FIG. 4. The vertical axis represents cAMP concentration, whereas the horizontal axis represents the added lipids or nucleotides. A set of four bars for each added sample from left to right respectively represents GPR34 (filled black), p2y5 (dotted), p2y9 (horizontally lined) and p2y10 (open white).
Figure 5:
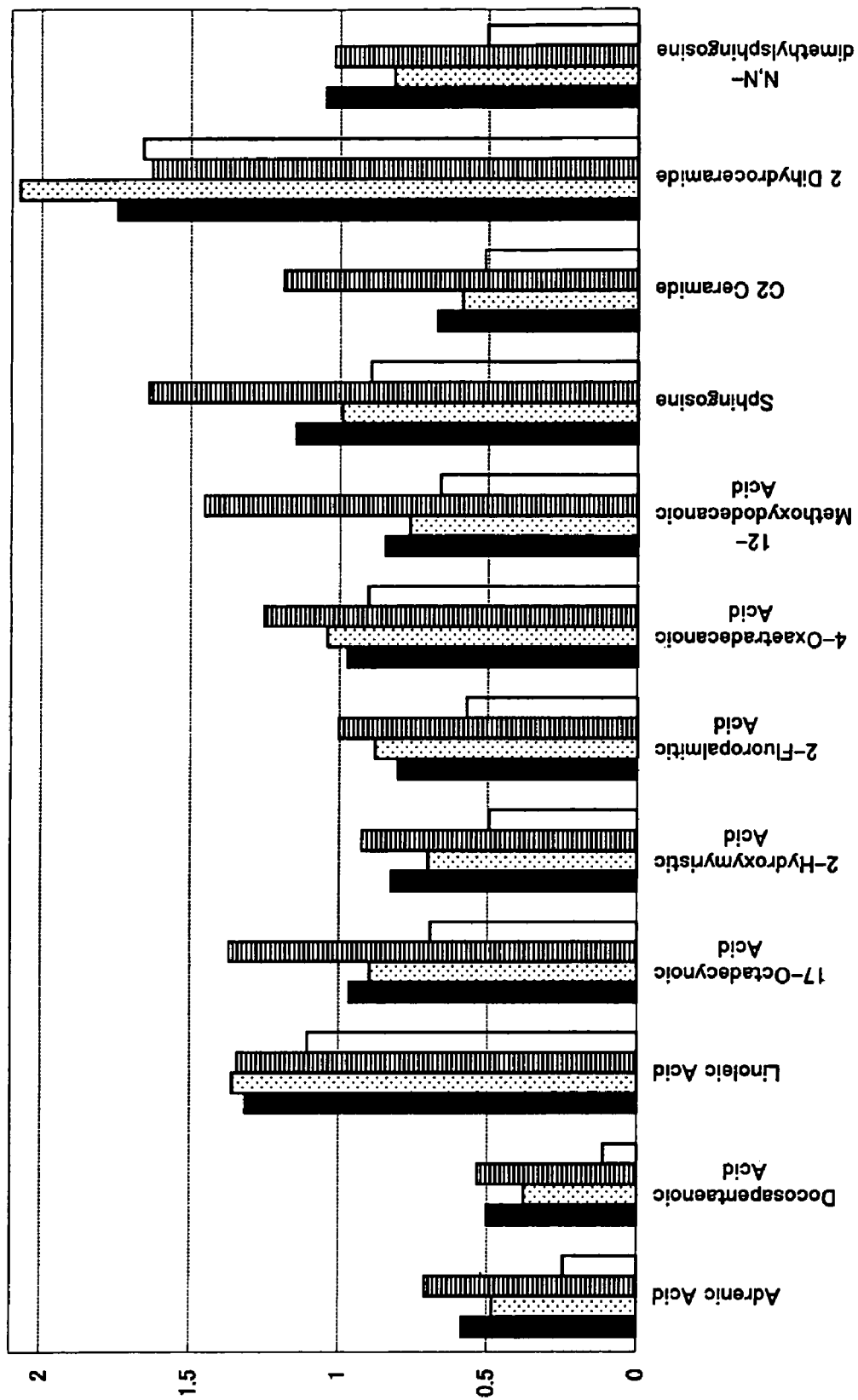
FIG. 5 shows the results of the changes in intracellular cAMP concentration by using independent CHO clones stably expressing four types of receptors such as GPR34, p2y5, p2y9 and p2y10 with addition of various kinds of lipids or nucleotides. The added lipids and nucleotides were as shown in FIG. 5. The vertical axis represents cAMP concentration, whereas the horizontal axis represents the added lipids or nucleotides. A set of four bars for each added sample from left to right respectively represents GPR34 (filled black), p2y5 (dotted), p2y9 (horizontally lined) and p2y10 (open white).
Figure 6:
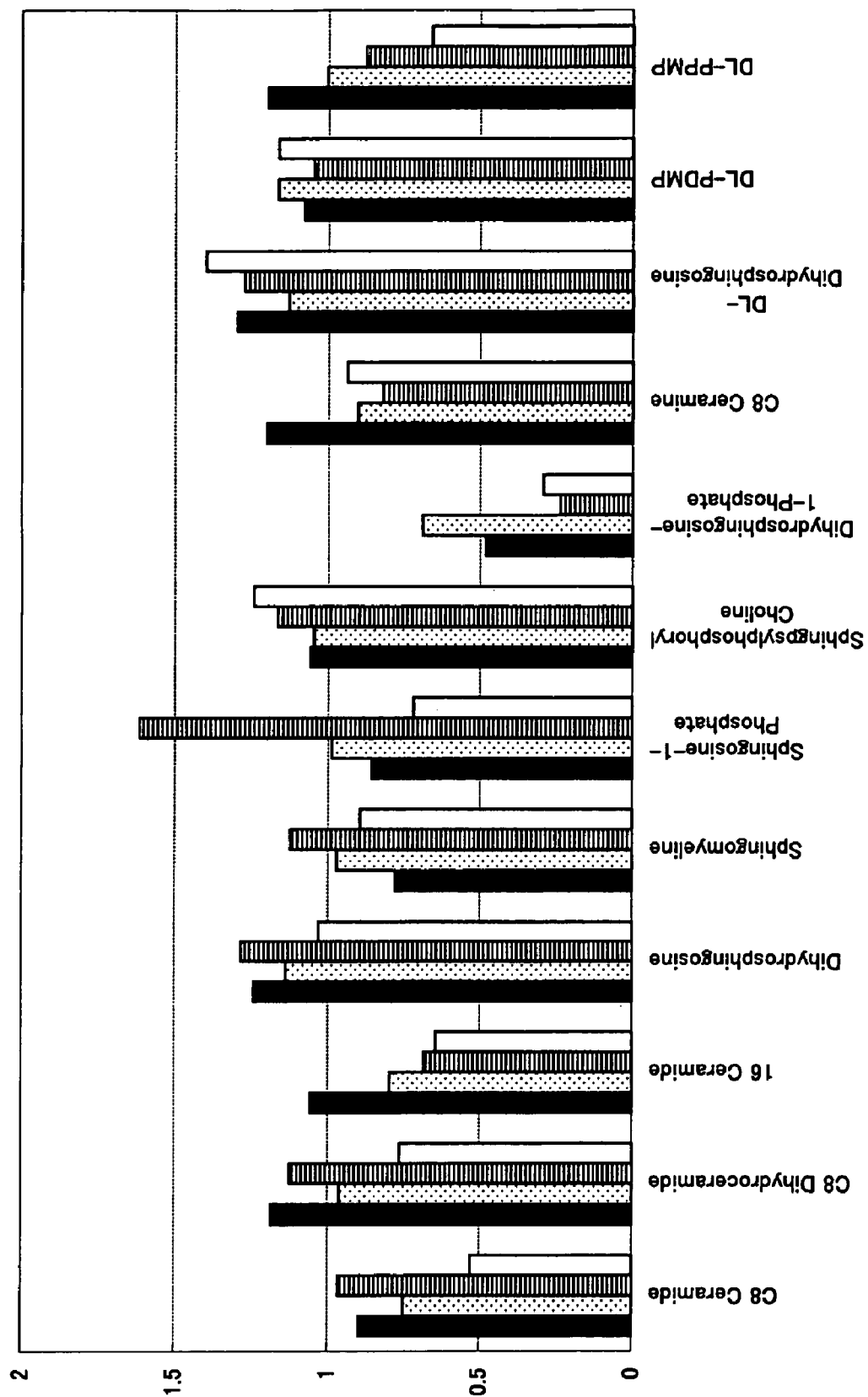
FIG. 6 shows the results of the changes in intracellular cAMP concentration by using independent CHO clones stably expressing four types of receptors such as GPR34, p2y5, p2y9 and p2y10 with addition of various kinds of lipids or nucleotides. The added lipids and nucleotides were as shown in FIG. 6. The vertical axis represents CAMP concentration, whereas the horizontal axis represents the added lipids or nucleotides. A set of four bars for each added sample from left to right respectively represents GPR34 (filled black), p2y5 (dotted), p2y9 (horizontally lined) and p2y10 (open white).
Figure 7:
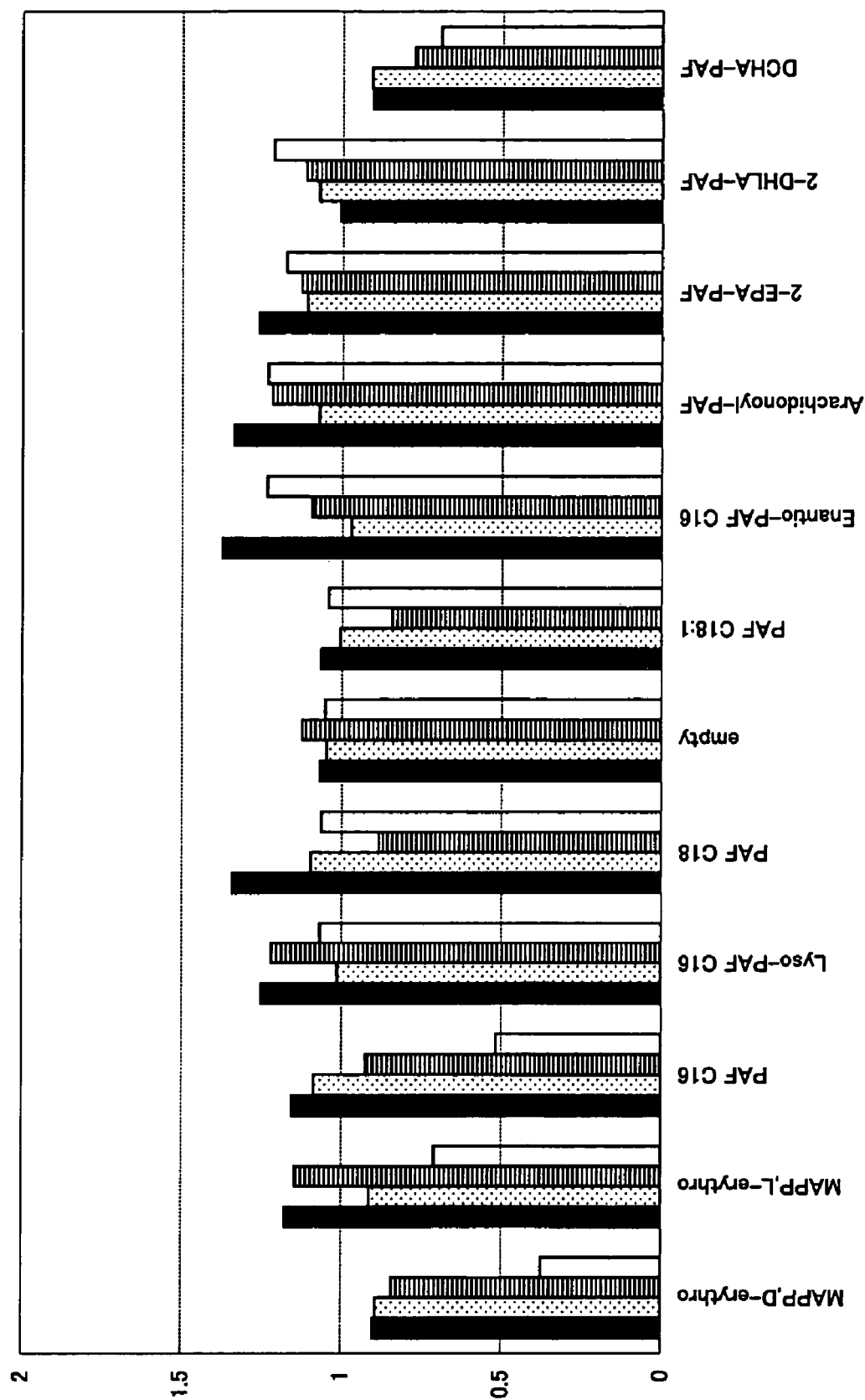
FIG. 7 shows the results of the changes in intracellular cAMP concentration by using independent CHO clones stably expressing four types of receptors such as GPR34, p2y5, p2y9 and p2y10 with addition of various kinds of lipids or nucleotides. The added lipids and nucleotides were as shown in FIG. 7. The vertical axis represents cAMP concentration, whereas the horizontal axis represents the added lipids or nucleotides. A set of four bars for each added sample from left to right respectively represents GPR34 (filled black), p2y5 (dotted), p2y9 (horizontally lined) and p2y10 (open white).

FIG. 3 shows the result of close investigation regarding the LPA (10 μM)-induced calcium concentration changes in each cell by using CHO clones of each receptors. The vertical axis in FIG. 3 shows a calcium concentration (RFU), whereas the horizontal axis shows time (sec) The closed circle (●) in FIG. 3 represents GPR 34, open square (□) represents p2y5, open triangle (Δ) represents p2y9 and (x) represents p2y10 respectively.

As apparent from the above result, LPA at a concentration of 10 μM induced an increase in calcium concentration specifically in p2y9 only. LPA was thus found to be a ligand of p2y9.

Then, the changes in intracellular cyclic AMP (cAMP) concentration were monitored respectively using CHO clones stably expressing four types of receptors. The reaction was carried out at room temperature for 30 minutes by using 59 types of lipids selected from Lipid Library of BIOMOL and 17 types of nucleotides.

Figure 10:
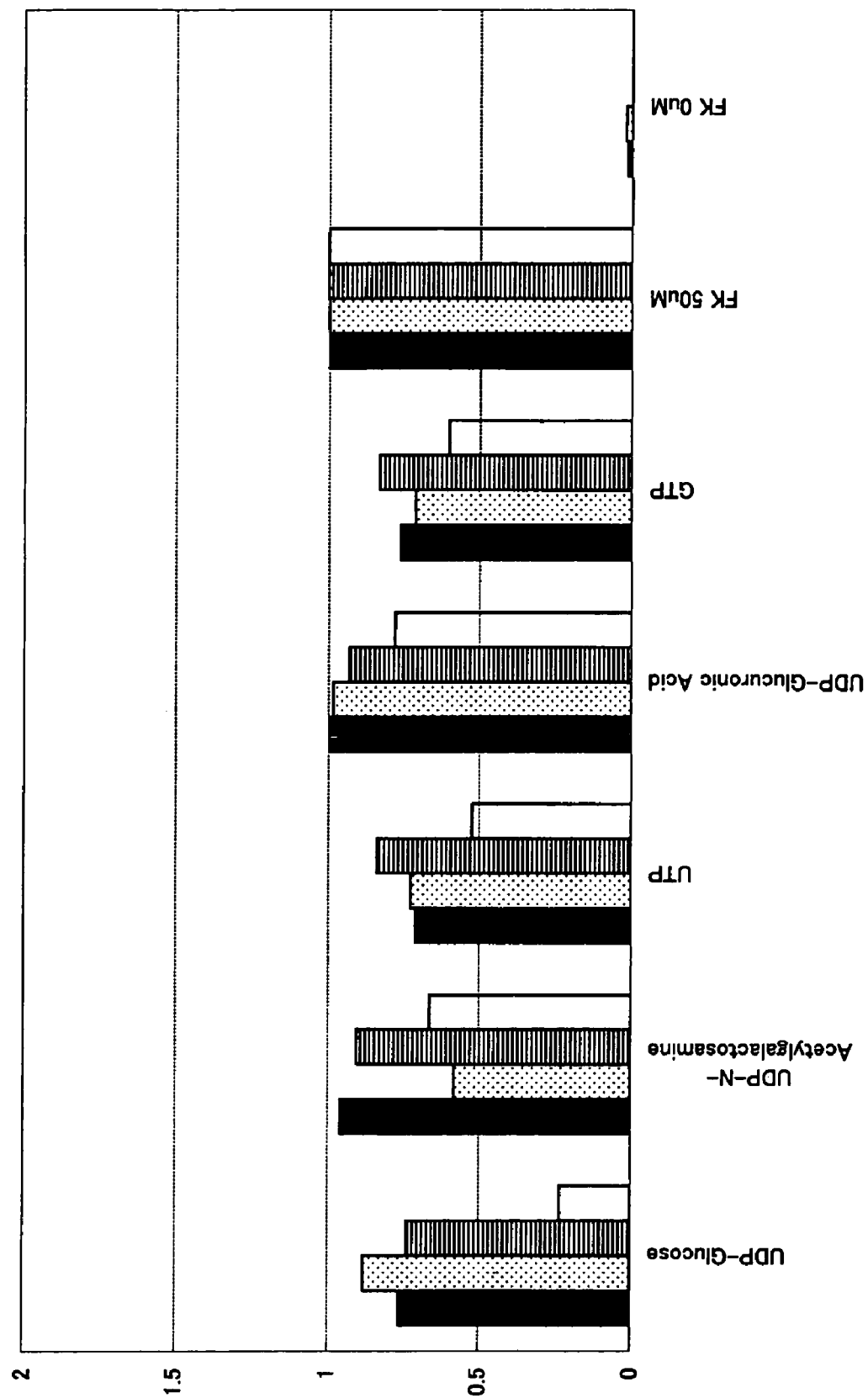
FIG. 10 shows the results of the changes in intracellular cAMP concentration by using independent CHO clones stably expressing four types of receptors such as GPR34, p2y5, p2y9 and p2y10 with addition of various kinds of lipids or nucleotides. The added lipids and nucleotides were as shown in FIG. 10. The vertical axis represents cAMP concentration, whereas the horizontal axis represents the added lipids or nucleotides. A set of four bars for each added sample from left to right respectively represents GPR34 (filled black), p2y5 (dotted), p2y9 (horizontally lined) and p2y10 (open white). The bars at far right of FIG. 10 represent control.

The results were shown in FIGS. 4 to 10. The used lipids and nucleotides were as shown in FIGS. 4 to 10 respectively. The vertical axis in each graph represents cAMP concentration, whereas the horizontal axis represents added lipids or nucleotides. The bars at far right in FIG. 10 represent control. A set of four bars for individual samples in the graphs from left to right respectively represents GPR34 (filled black), p2y5 (dotted), p2y9 (horizontally lined) and p2y10 (open white).

Figure 8:
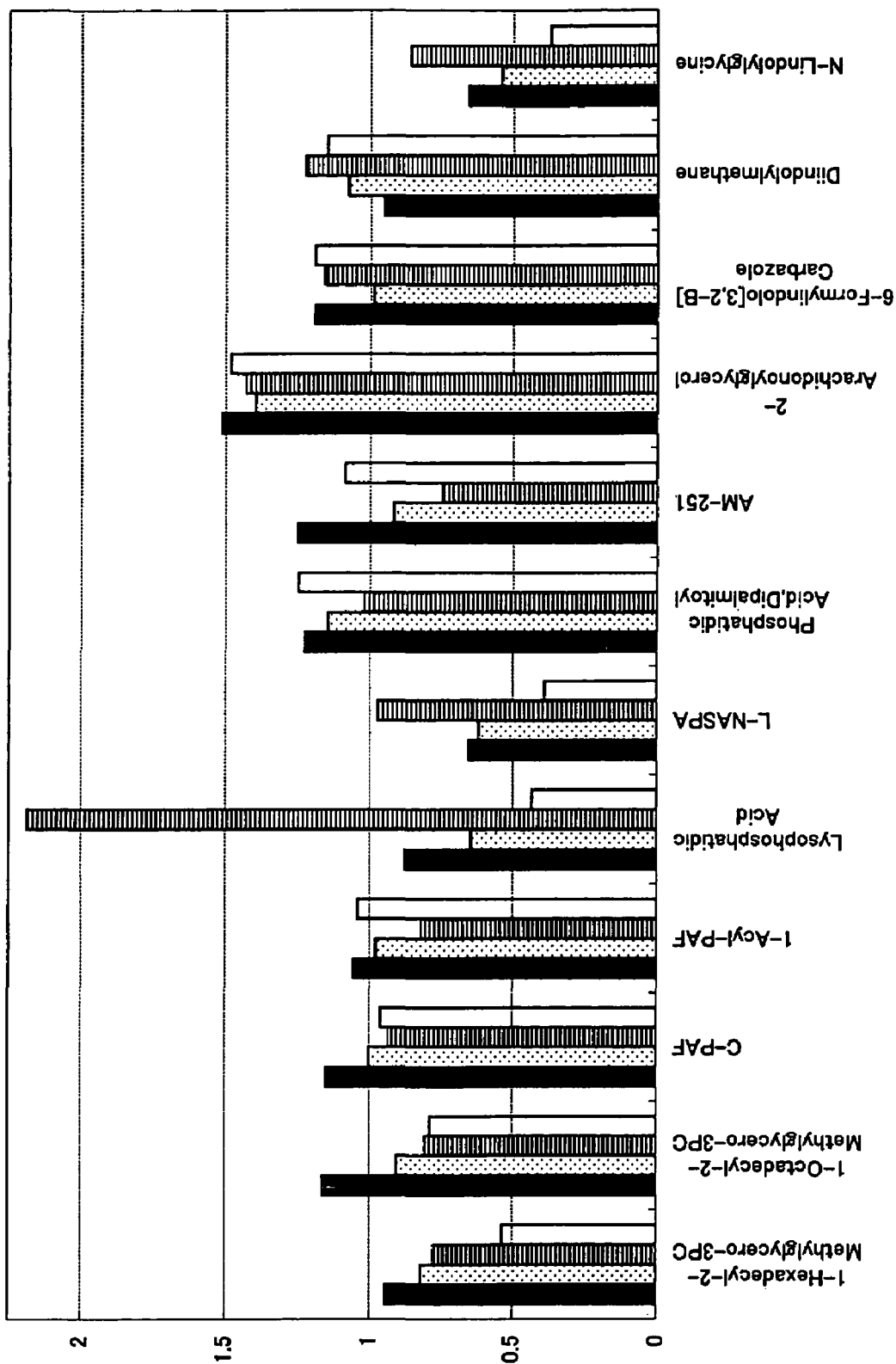
FIG. 8 shows the results of the changes in intracellular cAMP concentration by using independent CHO clones stably expressing four types of receptors such as GPR34, p2y5, p2y9 and p2y10 with addition of various kinds of lipids or nucleotides. The added lipids and nucleotides were as shown in FIG. 8. The vertical axis represents cAMP concentration, whereas the horizontal axis represents the added lipids or nucleotides. A set of four bars for each added sample from left to right respectively represents GPR34 (filled black), p2y5 (dotted), p2y9 (horizontally lined) and p2y10 (open white). The fifth sample from the left in FIG. 8 represents the case of LPA.
Figure 9:
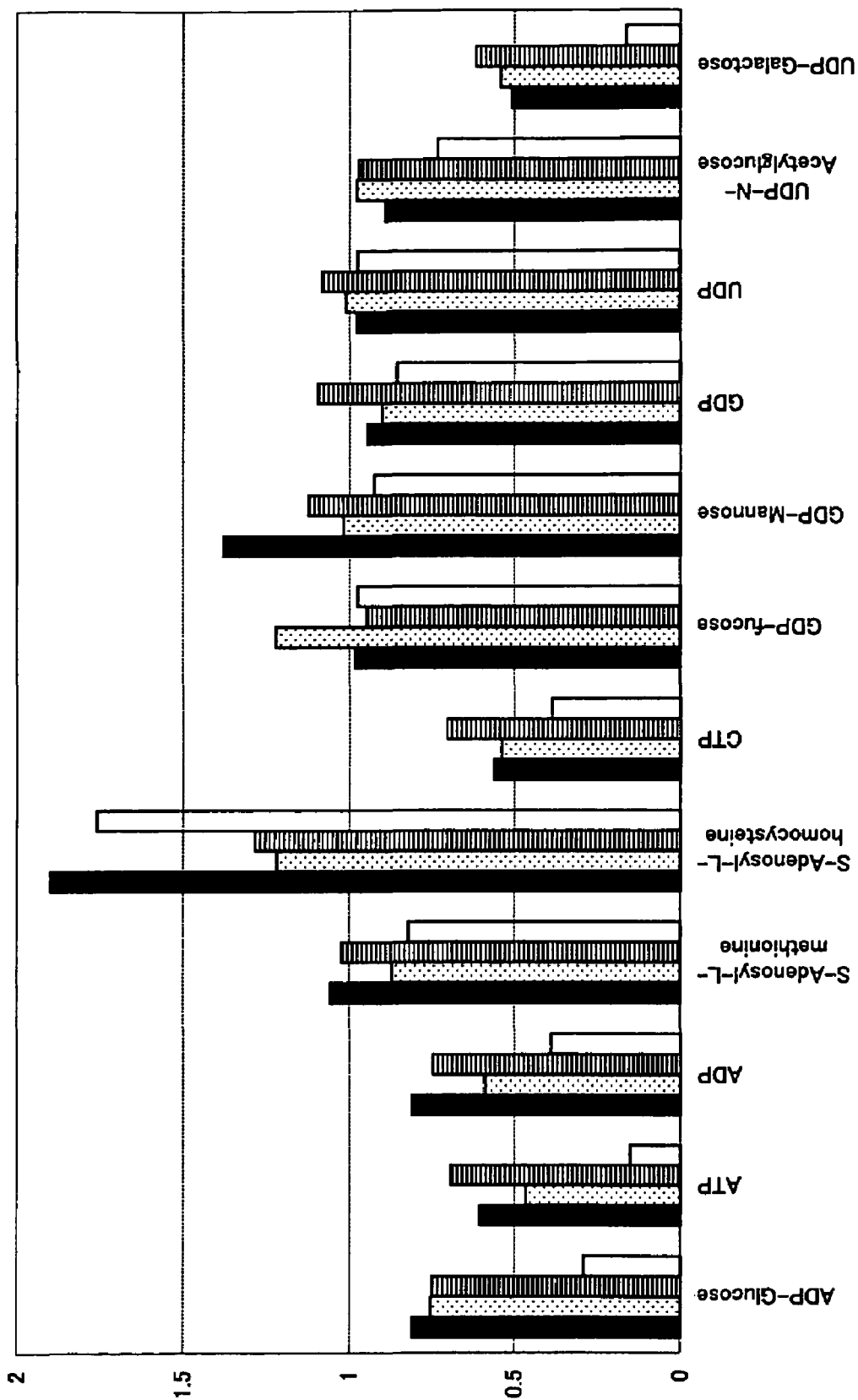
FIG. 9 shows the results of the changes in intracellular cAMP concentration by using independent CHO clones stably expressing four types of receptors such as GPR34, p2y5, p2y9 and p2y10 with addition of various lipids or nucleotides. The added lipids and nucleotides were as shown in FIG. 9. The vertical axis represents cAMP concentration, whereas the horizontal axis represents the added lipids or nucleotides. A set of four bars for each added sample from left to right respectively represents GPR34 (filled black), p2y5 (dotted), p2y9 (horizontally lined) and p2y10 (open white).

As shown in the fifth sample from the left in FIG. 8, p2y9 stimulated with LPA exhibited a significant increase in cAMP concentration.

Then the investigation with respect to CHO clone has been carried out. Experiment of calcium incorporation was conducted in four independent CHO clones, #01, #09, #15 and #20, stably expressing p2y9. The changes in intracellular calcium concentration due to the addition of various concentrations of LPA were measured. As a negative control, CHO cells which acquired neomycin resistance by transfected only with pCXN2.1 vector were used.

Figure 11:
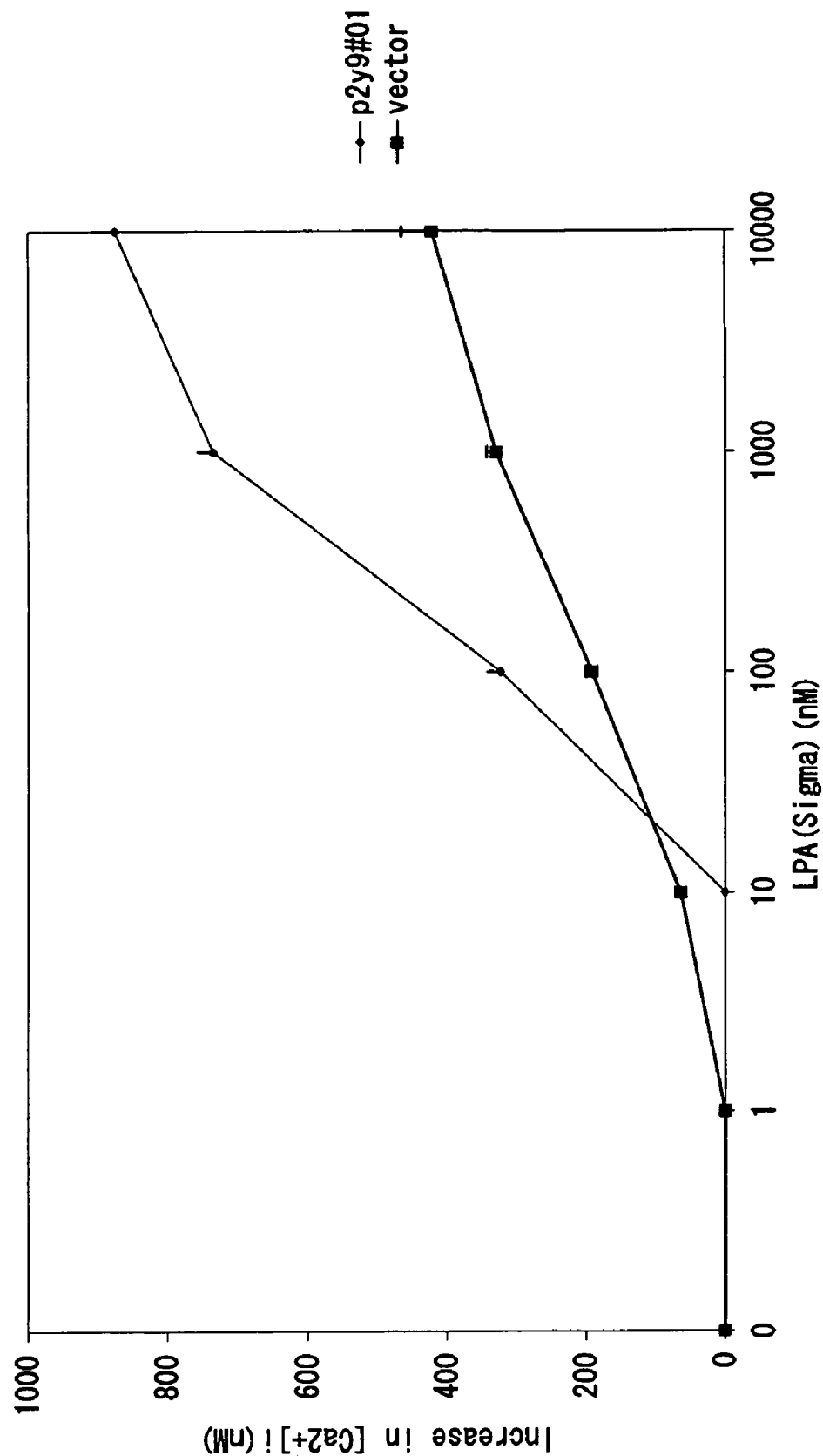
FIG. 11 shows the results of the changes in intracellular calcium concentration of #01 out of four independent CHO clones (i.e. #01, #09, #15 and #20) stably expressing p2y9 with addition of various concentrations of LPAs. The horizontal axis represents the concentration of LPA (nM), whereas the vertical axis represents the increase in calcium concentration (nM). The closed diamond (◆) in FIG. 11 represents each clone and the closed square (■) represents the negative control.
Figure 12:
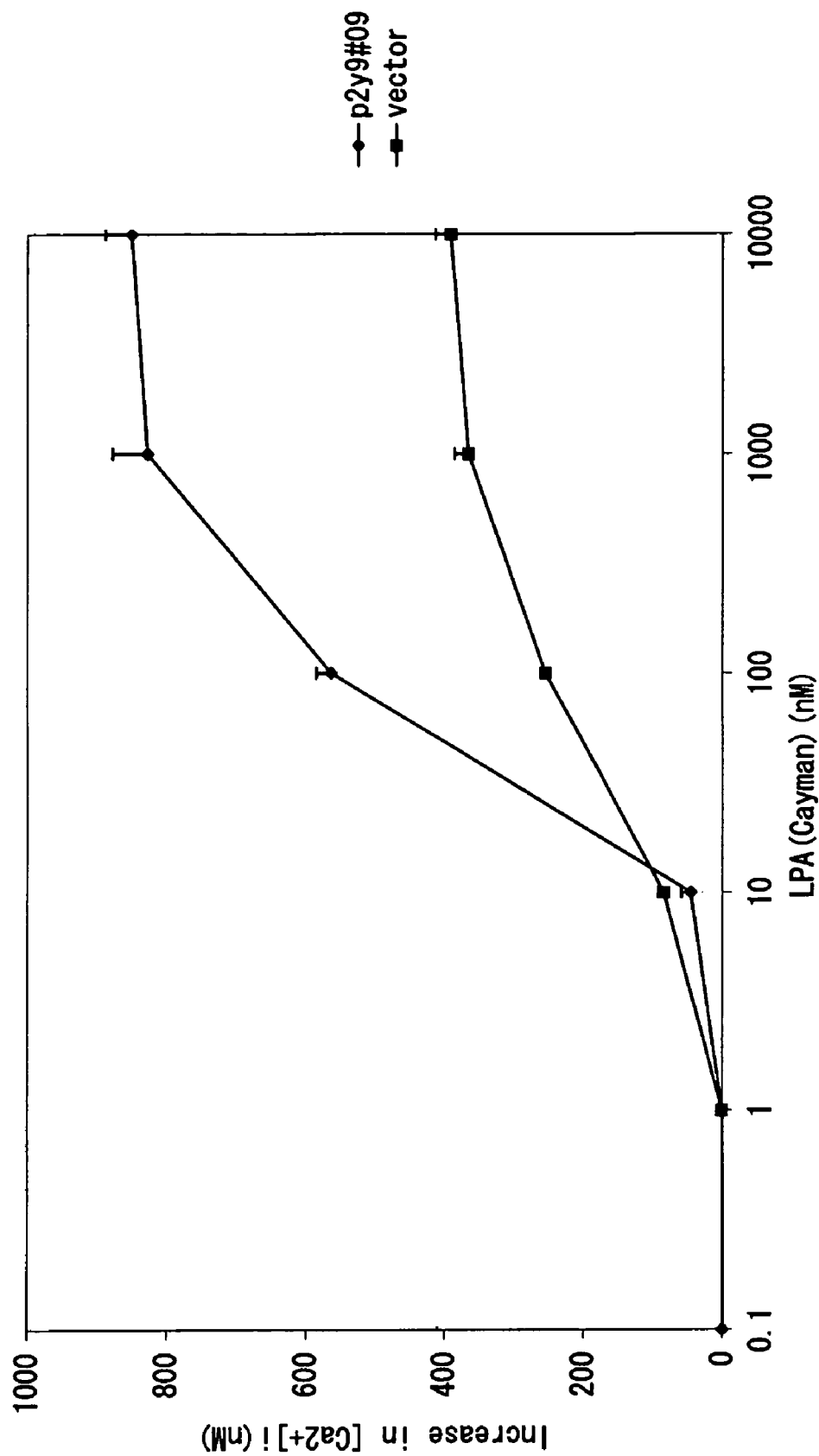
FIG. 12 shows the results of the changes in intracellular calcium concentration of #09 out of four independent CHO clones stably expressing p2y9 with addition of various concentrations of LPAs. The horizontal axis represents the concentration of LPA (nM), whereas the vertical axis represents the increase in calcium concentration (nM). The closed diamond (◆) in FIG. 12 represents each clone and the closed square (■) represents the negative control.
Figure 13:
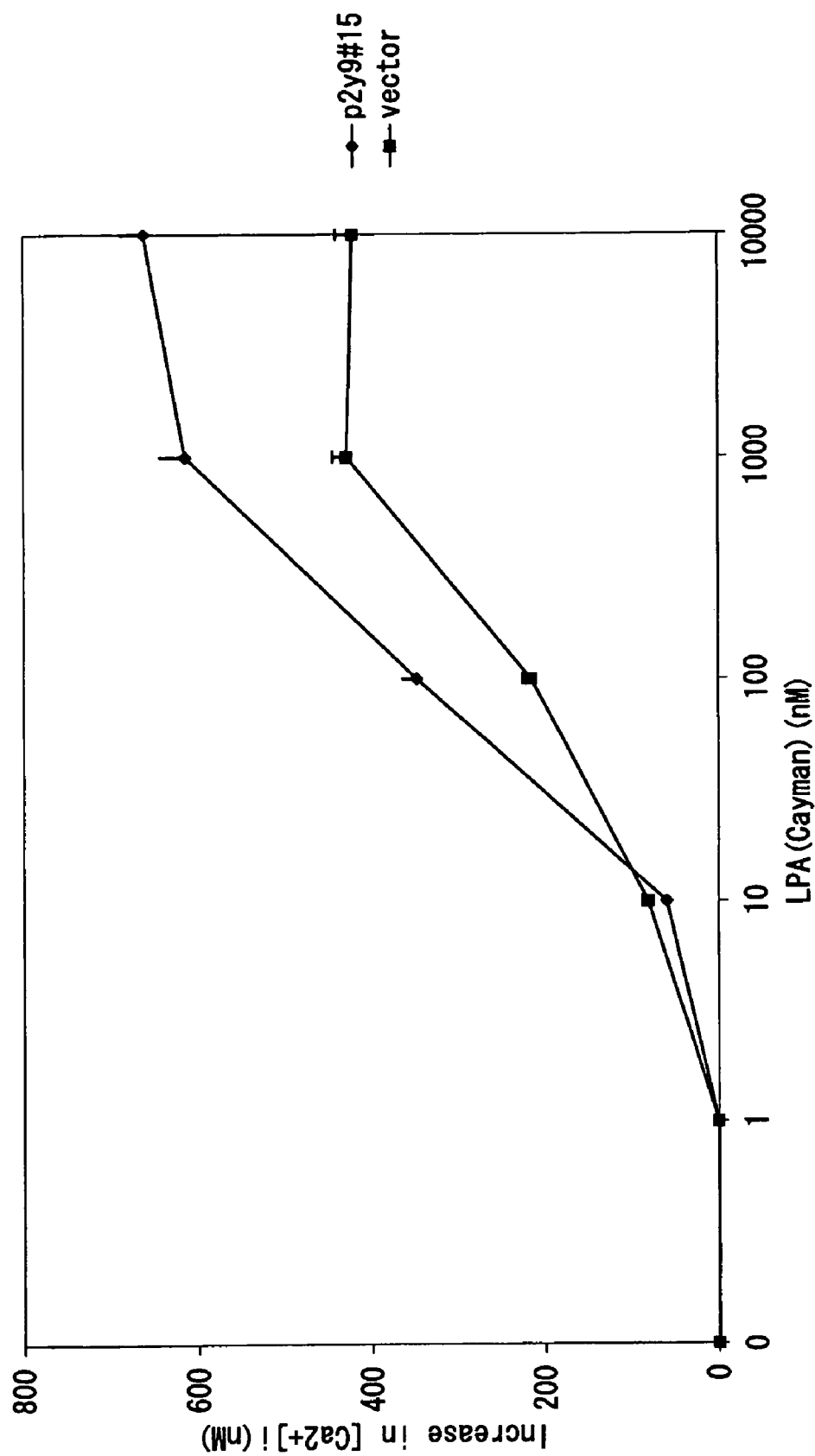
FIG. 13 shows the results of the changes in intracellular calcium concentration of #15 out of four independent CHO clones stably expressing p2y9 with addition of various concentrations of LPAs. The horizontal axis represents the concentration of LPA (nM), whereas the vertical axis represents the increase in calcium concentration (nM). The closed diamond (◆) in FIG. 13 represents each clone and the closed square (■) represents the negative control.
Figure 14:
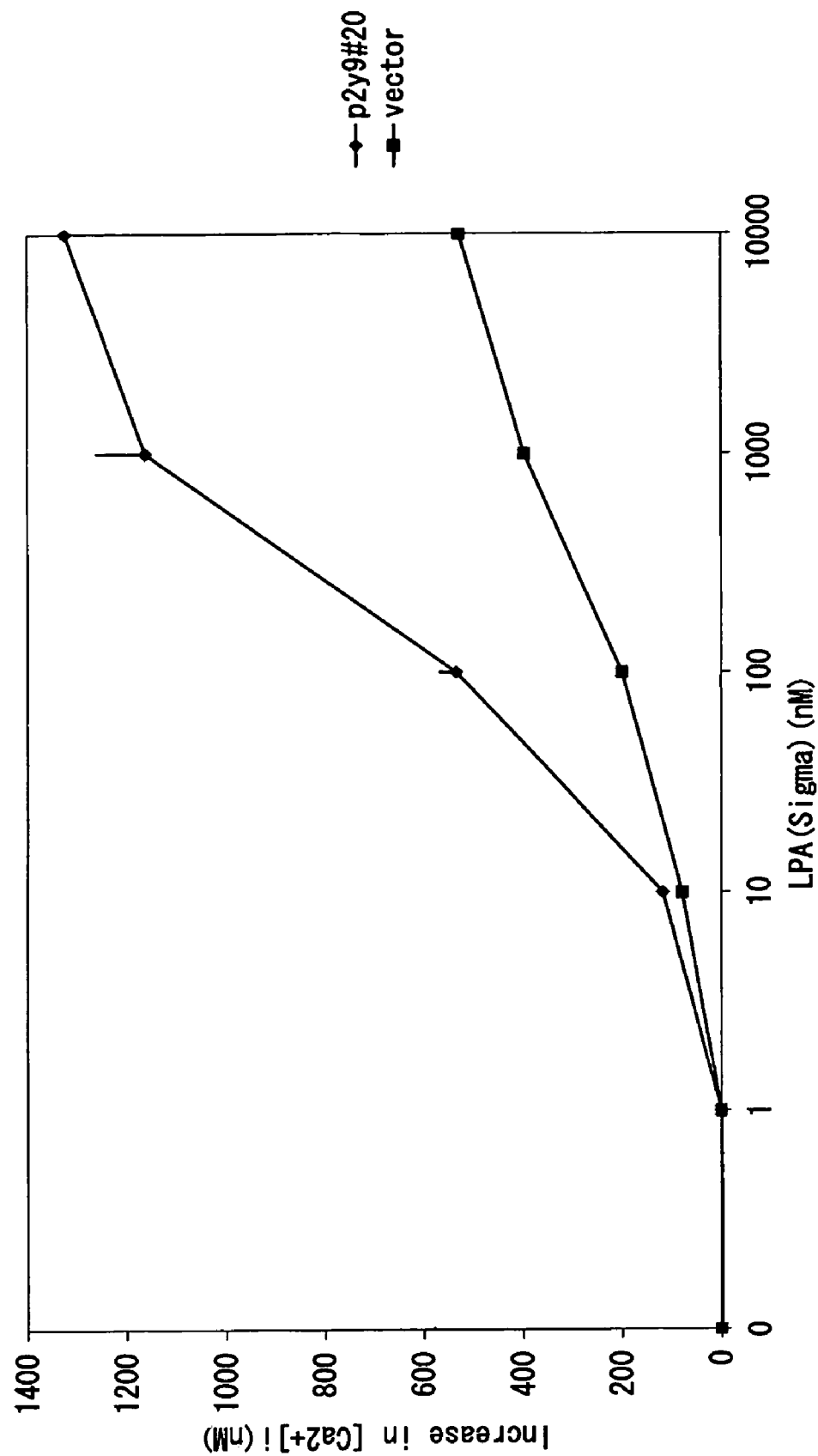
FIG. 14 shows the results of the changes in intracellular calcium concentration of #20 out of four independent CHO clones stably expressing p2y9 with addition of various concentrations of LPAs. The horizontal axis represents the concentration of LPA (nM), whereas the vertical axis represents the increase in calcium concentration (nM). The closed diamond (◆) in FIG. 14 represents each clone and the closed square (■), represents the negative control.

The results are shown in FIGS. 11 to 14. The horizontal axis in each graph represents the concentration of LPA (nM), whereas the vertical axis represents increase in calcium (nM) FIG. 11 shows the result of clone #01. FIG. 12 shows the result of clone #09. FIG. 13 shows the result of clone #15. FIG. 14 shows the result of clone #20. The closed diamond (♦) in FIGS. 11 to 14 represents the results of individual clones and the closed square (■) represents the results of negative controls.

Since LPA receptors are endogenously present in CHO cells, the cells transfected with empty vector exhibits reactivity with LPA. However, each clone transfected with p2y9 exhibited more significant increase in intracellular calcium concentration LPA concentration-dependently.

Figure 15:
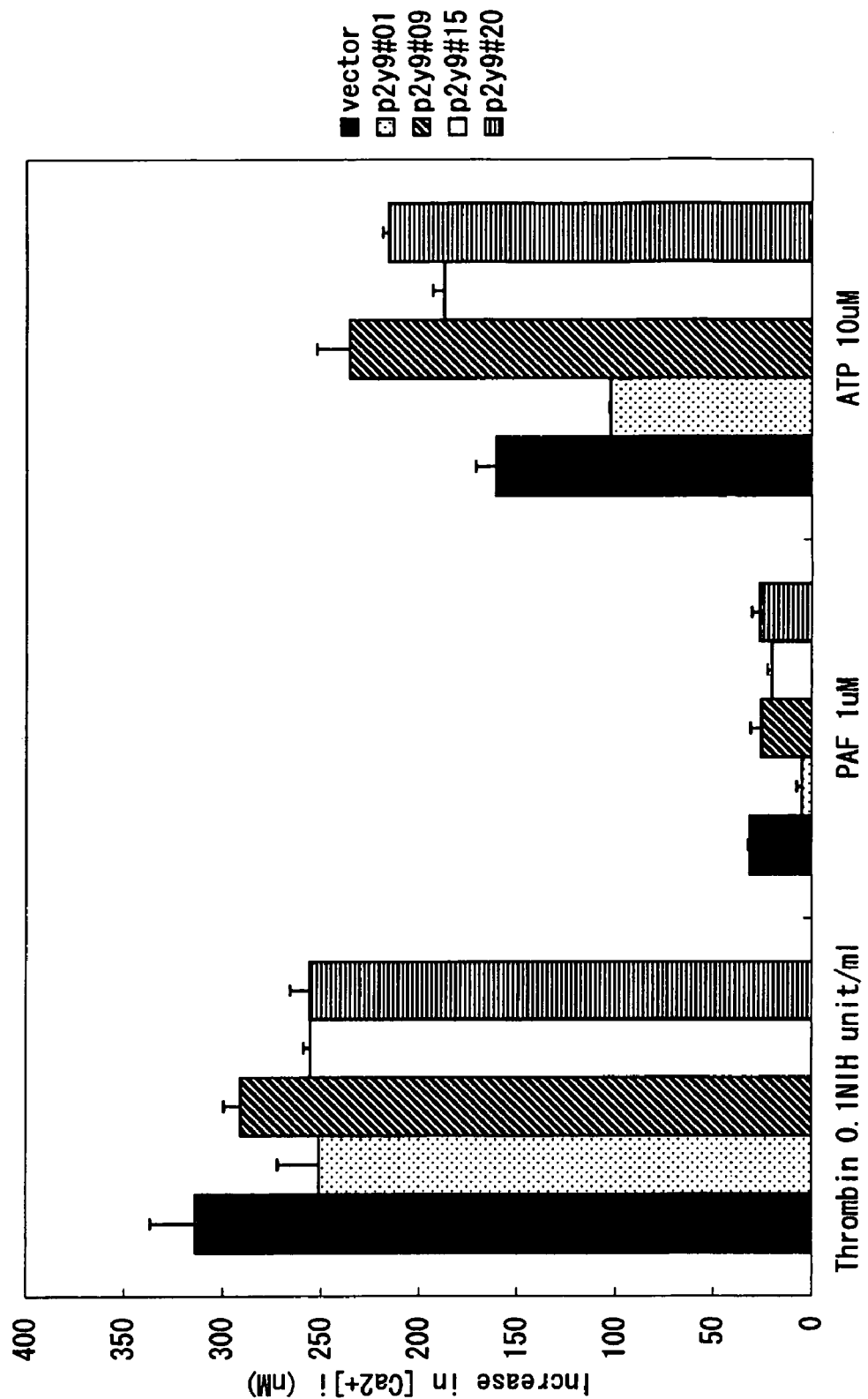
FIG. 15 shows the results of investigation on the changes in intracellular calcium concentration in four independent CHO clones (i.e. #01, #09, #15 and #20) induced by thrombin (0.1 NIH units/ml), PAF (1 μM) and ATP (10 μM). The vertical axis represents the increase in calcium concentration (nM), whereas horizontal axis represents each added sample. Each bar in a set of five bars from left to right respectively represents CHO cell whereto only a negative control vector is introduced, p2y9 clones of #01, #09, #15 and #20.

FIG. 15 shows the result of investigation, carried out in the same manner as the above, on the changes in intracellular calcium concentration induced by thrombin (0.1 NIH units/ml), PAF (1 μM) and ATP (10 μM). The vertical axis in FIG. 15 represents increase in calcium (nM), whereas horizontal axis represents added samples. A set of bars in the graph from left to right respectively represents negative control i.e. CHO cells transfected with empty vector (filled black), p2y9 clone #01 (dotted), p2y9 clone #09 (diagonally lined), p2y9 clone #15 (open white) and p2y9 clone #20 (horizontally lined).

Resultantly, no significant changes due to the addition of thrombin, PAF and ATP have been observed in both negative control and the cells transfected with p2y9.

CHO clones stably expressing p2y9 or p2y5 were treated with various concentrations of LPAs in the presence or absence of pertussis toxin (PTX) at room temperature for 30 min, and whereby intracellular cAMP concentrations were measured. As a negative control, CHO cells which acquired neomycin resistance by transfected only with pCXN2.1 vector were used.

Figure 16:
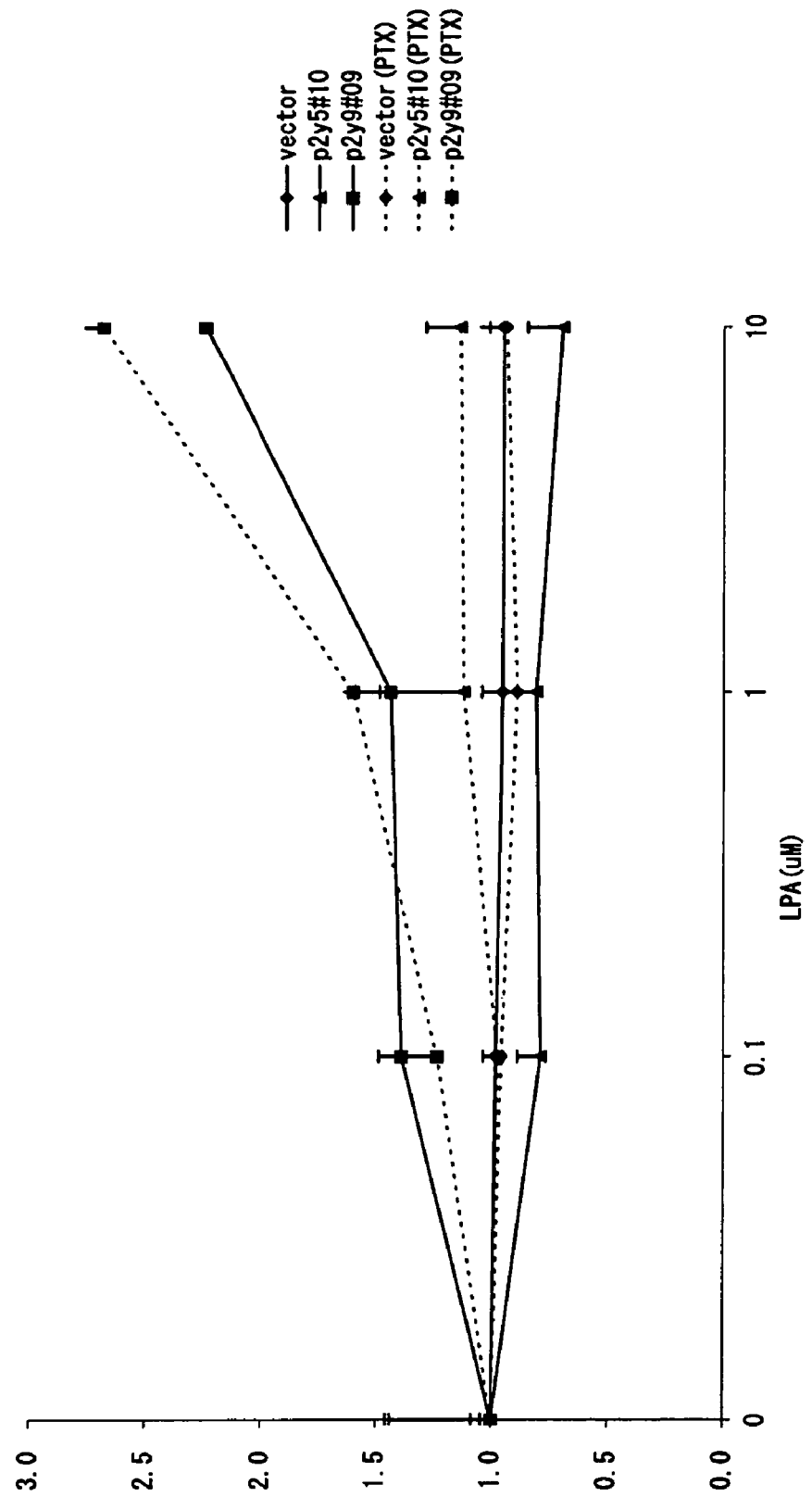
FIG. 16 shows the results of intracellular cAMP concentration changes measured by using clones of CHO cells stably expressing p2y9 or p2y5 with addition of various concentrations of LPAs in the presence or absence of pertussis toxin (PTX).
Figure 17:
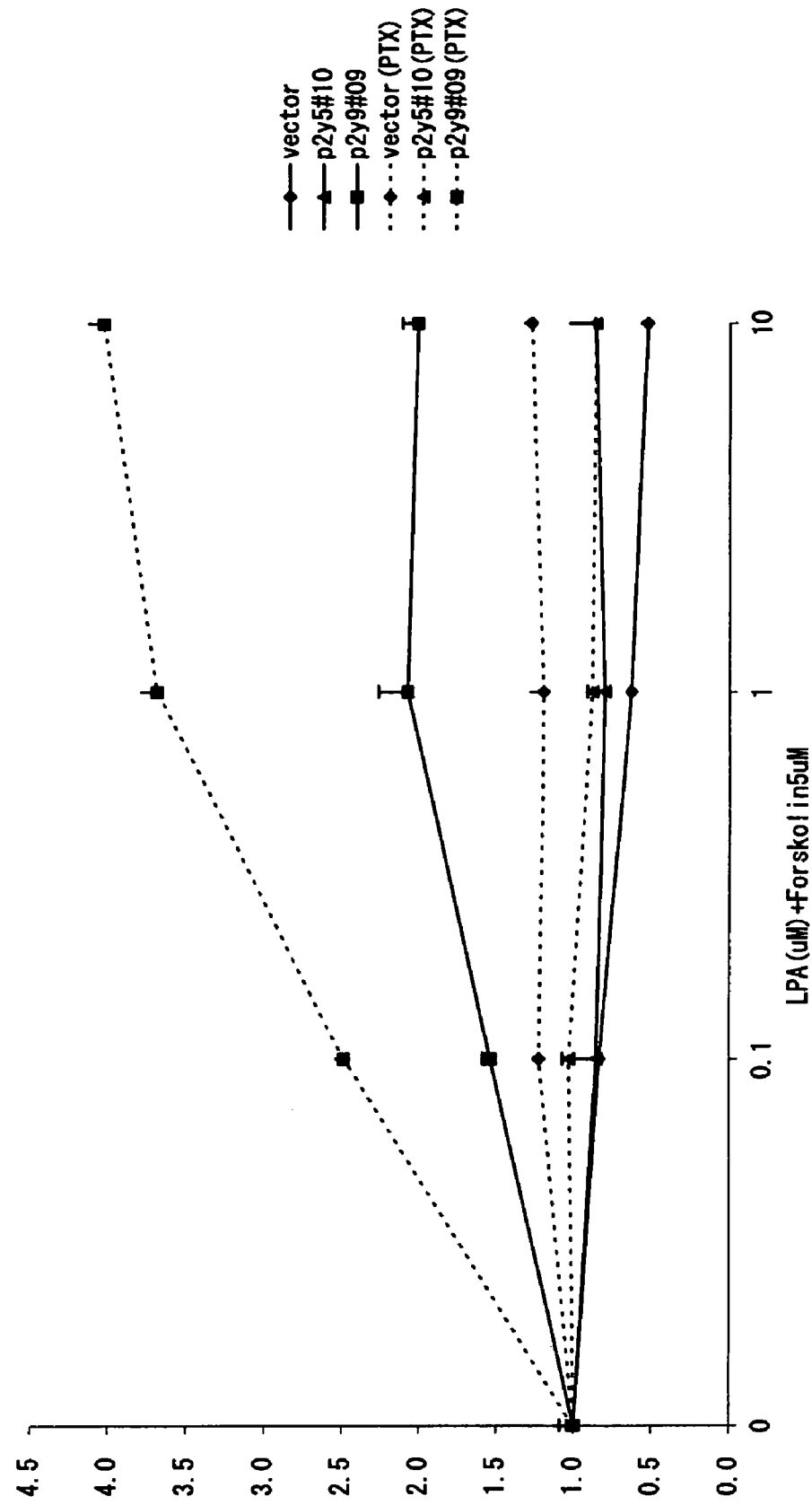
FIG. 17 shows the results of intracellular cAMP concentration changes measured by using clones of CHO cells stably expressing p2y9 or p2y5 with addition of various concentrations of LPAs in the presence or absence of pertussis toxin (PTX). The procedure was carried out in the same manner as described in FIG. 16 except for the treatment with forskolin (5 μM). The horizontal axis shows the concentration of LPA (nM), whereas the vertical axis shows the ratio of changes in cAMP concentration. The closed square (■) represents clone of p2y9, closed triangle (▲) represents clone of p2y5, closed diamond (◆) represents negative control i.e. a clone transfected with empty vector. The solid line shows the result in the absence of pertussis toxin (PTX), whereas the broken line shows the result in the presence of pertussis toxin (PTX).

The results were shown in FIGS. 16 and 17. FIG. 16 shows the result with no treatment with forskolin (5 μM), which induce increase in cAMP concentration. FIG. 17 shows the result treated with forskolin (5 μM). The horizontal axis shows the concentration of LPA (nM), whereas the vertical axis shows the ratio of changes in cAMP concentration. The closed square (■) represents clone of p2y9, closed triangle (▲) represents clone of p2y5, closed diamond (♦) represents negative control i.e. a clone transfected with empty vector. The solid line shows the result in the absence of pertussis toxin (PTX) whereas the broken line shows the result in the presence of pertussis toxin (PTX).

The results show that p2y9 induced an increase in cAMP concentration stimulated with LPA, but either p2y5 or negative control did not. In the presence of pertussis toxin (PTX) which is a suppressor of G protein Gi/Go, the increase in cAMP concentration was enhanced (shown in broken lines), presumably because LPA receptors endogenously present in CHO cells are sensitive to pertussis toxin (PTX) and have function to decrease a level of cAMP concentration. The LPA induced cAMP concentration in p2y9 was enhanced in the presence of forskolin (FIG. 16(B)).

p2y5 is 344-amino acid protein shares 56.2% homology with p2y9. FIG. 18 shows amino acid sequence comparison of both proteins. The sequence of p2y9 is displayed on top of the sequence of p2y5 with asterisks (*) indicating the matching amino acid residues. Although sequences of both proteins share higher homology, they are completely different in the reactivity with LPA. It is recognized that only p2y9 of the present invention among the proteins sharing homology with the platelet activating factor receptors (PAFR) (located in the left in the phylogenetic tree shown in FIG. 1) exhibited a specific reactivity against LPA.

LPA receptors are endogenously present in CHO cells, however then, the cells without expressing LPA receptors were used for monitoring reactivity toward LPA by introducing there into the genes of p2y9. RH7777 cells or B103 cells, not endogenously expressing LPA receptors, were used.

The cell-derived membrane fractions transiently expressing receptors were obtained by transfecting RH7777 Cells or B103 cells with pCXN2.1 vector whereto DNA encoding HA-tagged p2y9 or p2y5 were introduced. As negative controls, cells transfected only with pCXN2.1 vector instead of DNA encoding the receptor, were used. The membrane fractions were mixed with 1 nM, 3 nM or 10 nM of tritium labeled LPA and reacted at 4° C. for 60 minutes in order to obtain total bindings in respective concentrations. In parallel to this, in order to obtain the nonspecific bindings in respective concentrations, membrane fractions were also reacted with tritium labeled LPAs in the reaction mixture containing a 500-fold concentration of unlabeled LPA. The reaction mixture was filtrated by GF/C glass filter (Packard). The radioactivity that remained on the glass filter was determined as the volume of tritium labeled LPA binding with receptors. The specific binding value was calculated by subtracting the nonspecific binding value from the total binding value.

Figure 19:
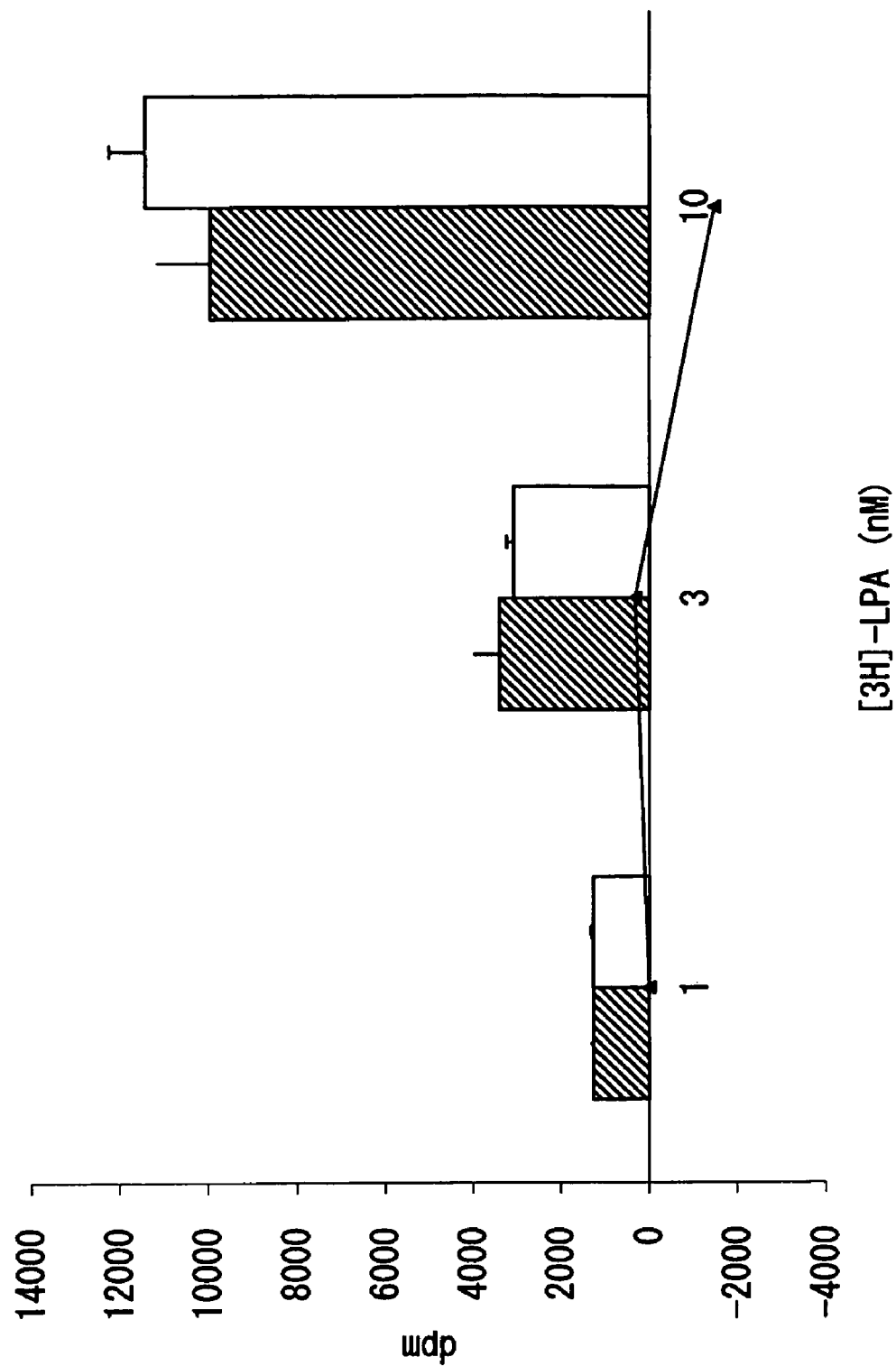
FIG. 19 shows the binding characteristics of LPA respectively with negative control, p2y5 and p2y9 measured by using RH7777 cells transfected with p2y5, or p2y9 of the present invention.
Figure 20:
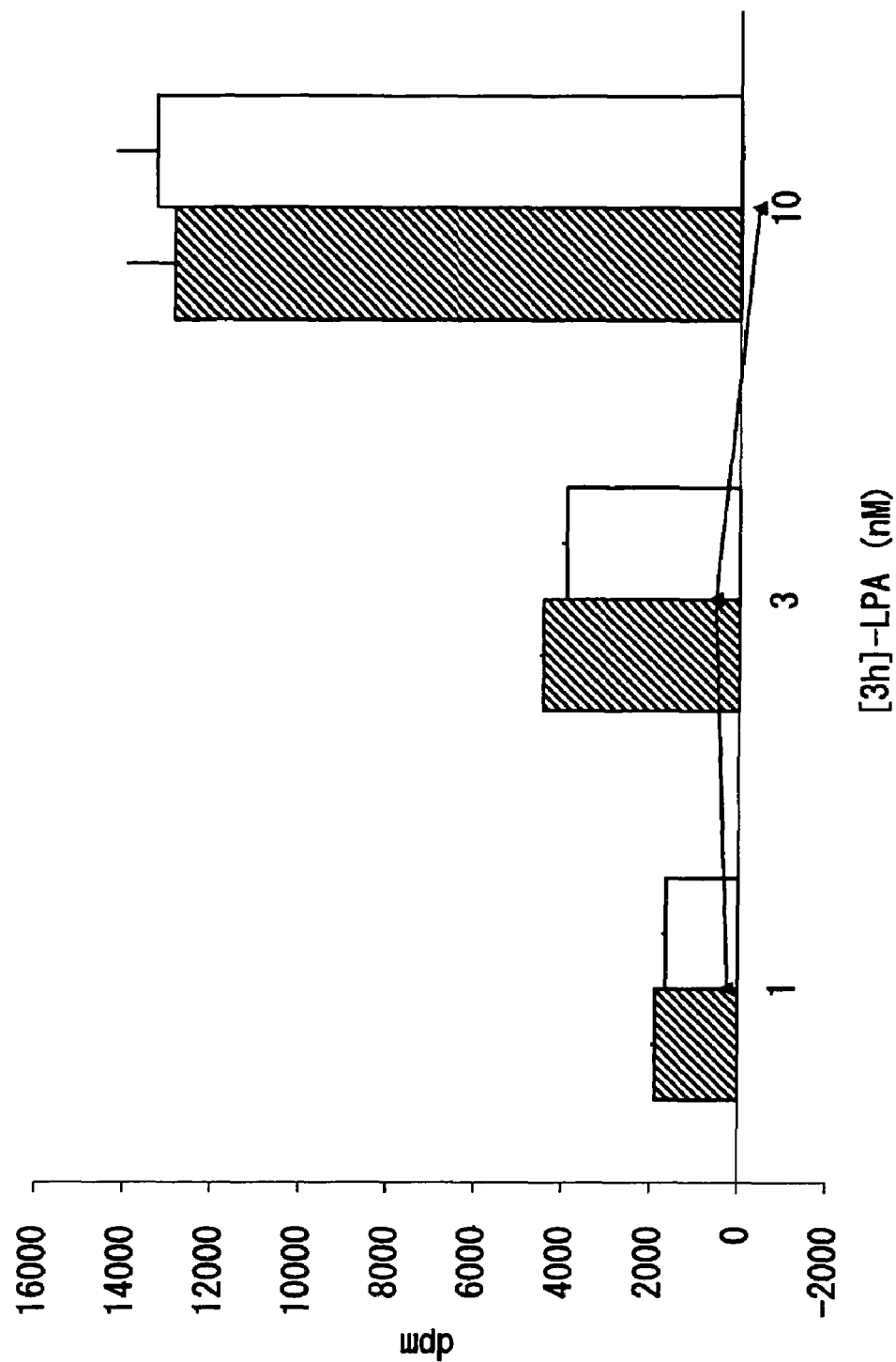
FIG. 20, the same as FIG. 19, shows the binding characteristics of LPA measured by using RH7777 cells transfected with p2y5, or p2y9 of the present invention.
Figure 21:
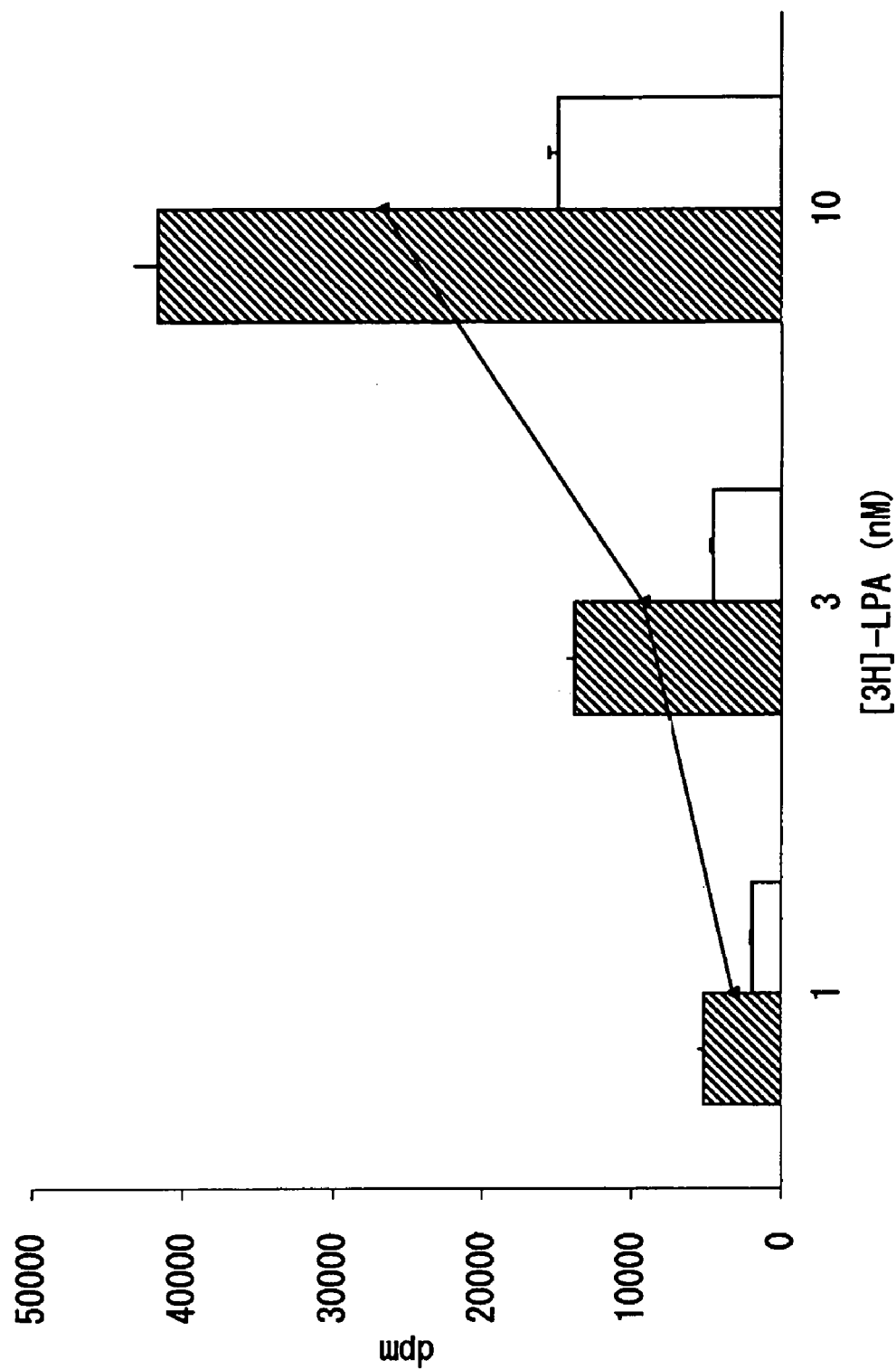
FIG. 21, the same as FIG. 19, shows the binding characteristics of LPA measured by using RH7777 cells transfected with p2y5, or p2y9 of the present invention.
Figure 22:
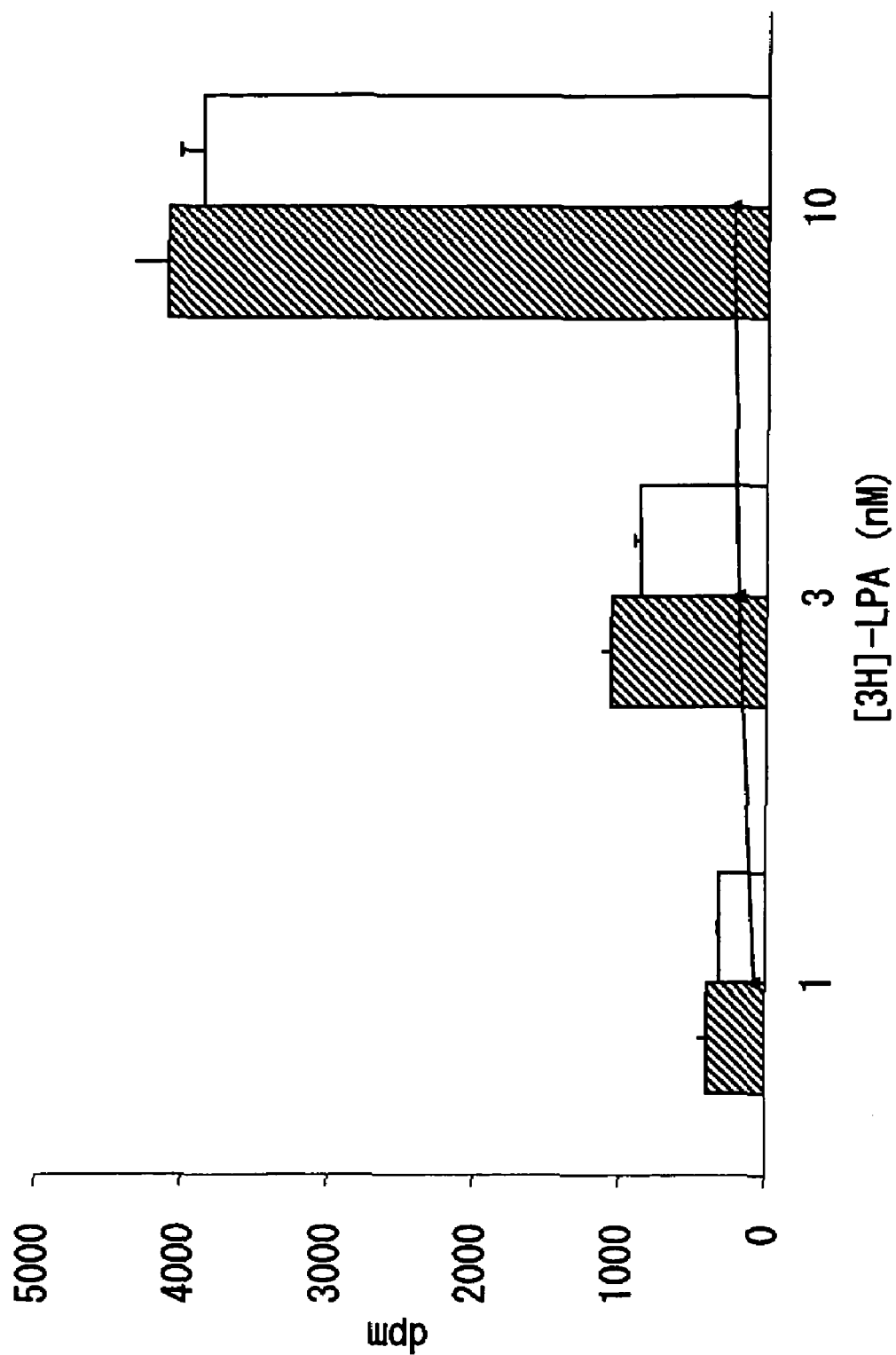
FIG. 22 shows the binding characteristics of LPA respectively with negative control, p2y5 and p2y9 measured by using B103 cells transfected with p2y5, or p2y9 of the present invention.
Figure 23:
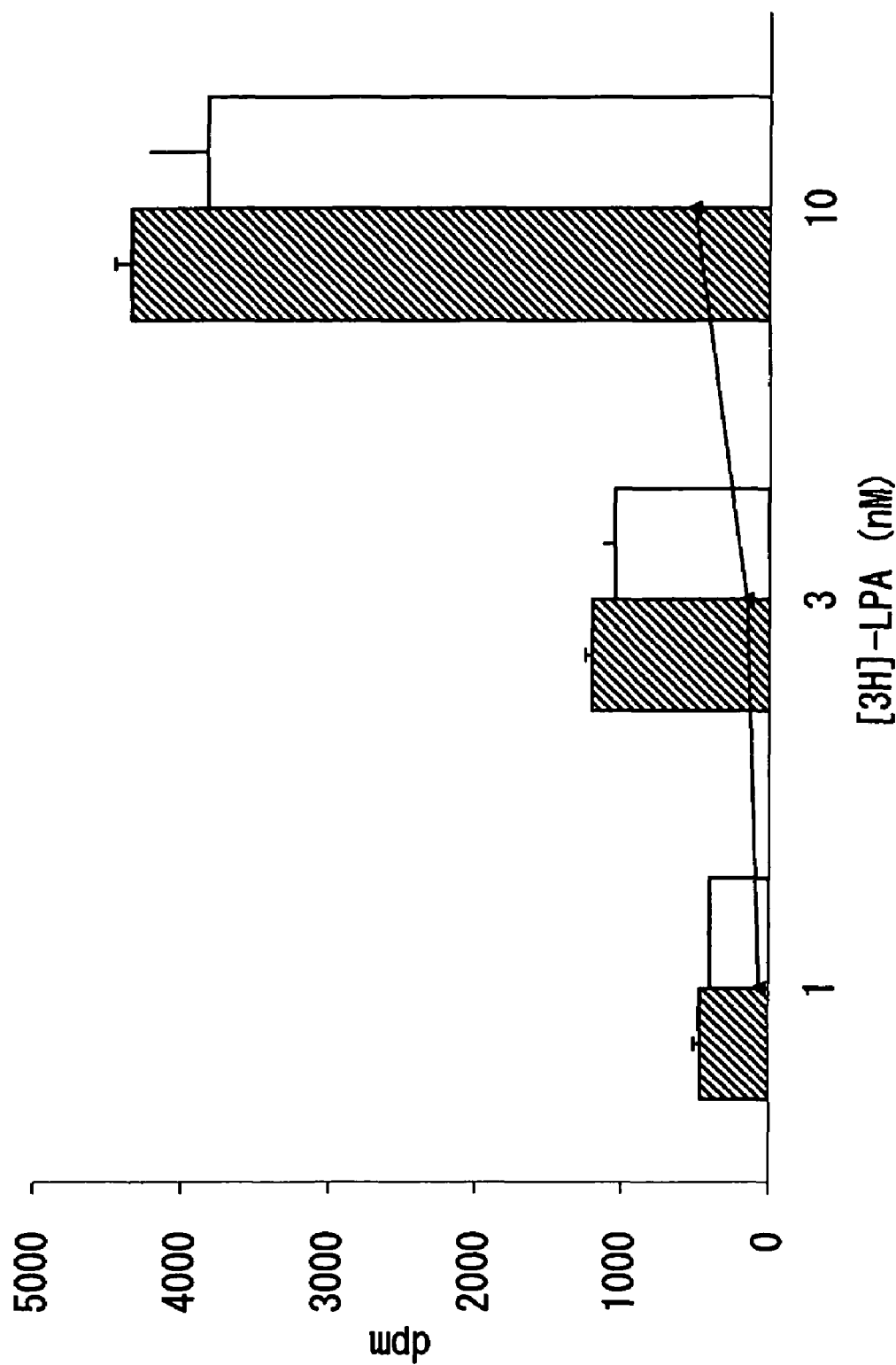
FIG. 23, the same as FIG. 22, shows the binding characteristics of LPA measured by using B103 cells transfected with p2y5, or p2y9 of the present invention.
Figure 24:
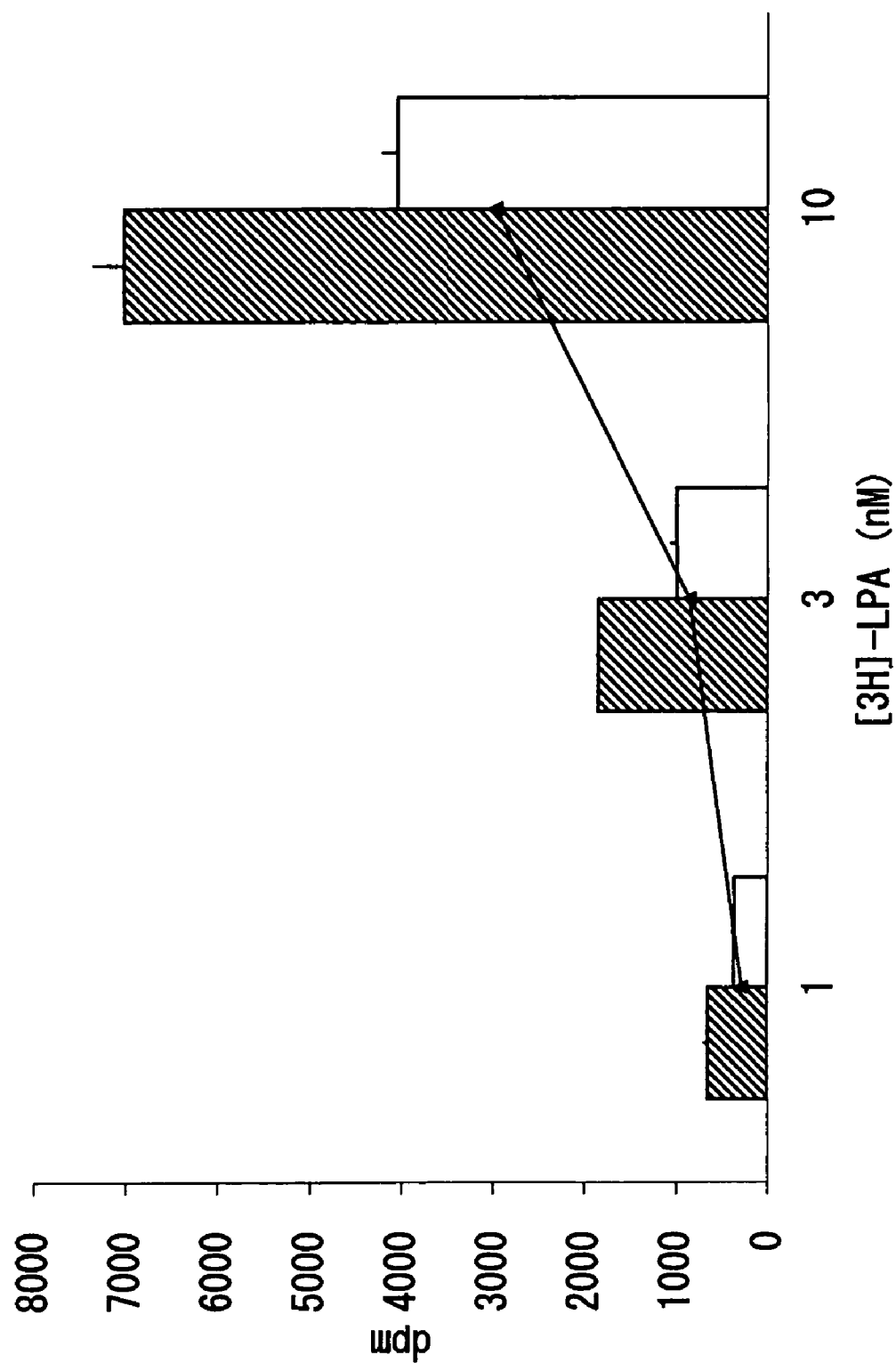
FIG. 24, the same as FIG. 22, shows the binding characteristics of LPA measured by using B103 cells transfected with p2y5, or p2y9 of the present invention.

The results are shown in FIGS. 19 to 21, and FIGS. 22 to 24. FIGS. 19 to 21 show the results with RH7777 cells, whereas FIGS. 22 to 24 show the results with B103 cells. FIGS. 19 to 21 show the results with negative controls, whereas FIGS. 19 and 22 show the results with negative controls, FIGS. 20 and 23 show the results with p2y5, FIGS. 21 and 24 show the results with p2y9 respectively. The horizontal axis in each graph shows the added tritium labeled LPA (nM), whereas the vertical axis shows the detected radiation (dpm). The diagonally lined bar in the graph represents total bindings, the white (open) bar on the right represents nonspecific bindings and the closed triangle (▲) represents the specific bindings obtained by subtracting the nonspecific bindings from the total bindings.

As a result, it was found that p2y9 expressed in any cells specifically bind to LPA.

P2y9 was further evaluated in the reactivity with other lipids by using the transfected RH7777 cell-derived membrane fractions transiently expressing receptors.

The membrane fractions obtained as above were mixed with 5 nM of tritium labeled LPA and reacted at 4° C. for 60 minutes. The obtained total bindings of LPA alone was used as control (the value was indicated as "buffer" in FIG. 25). In parallel to this, 5 nM of tritium labeled LPA independently containing 1 µM of unlabeled lipids (LPC: lysophosphatidylcholine, LPE: lysophosphatidylethanolamine, LPS: lysophosphatidylserine, LPG; lysophosphatidylglycerol, PA: phosphatidyic acid, PAF: platelet activating factor, S1P: sphingosine-1-phosphate, SPC: sphyngosylphosphocholine) was reacted in the same manner.

After termination of the reaction, the reaction mixture was filtrated by GF/C glass filter (Packard). The radioactivity that remained on the glass filter was determined as the volume of tritium labeled LPA binding with receptors.

Figure 25:
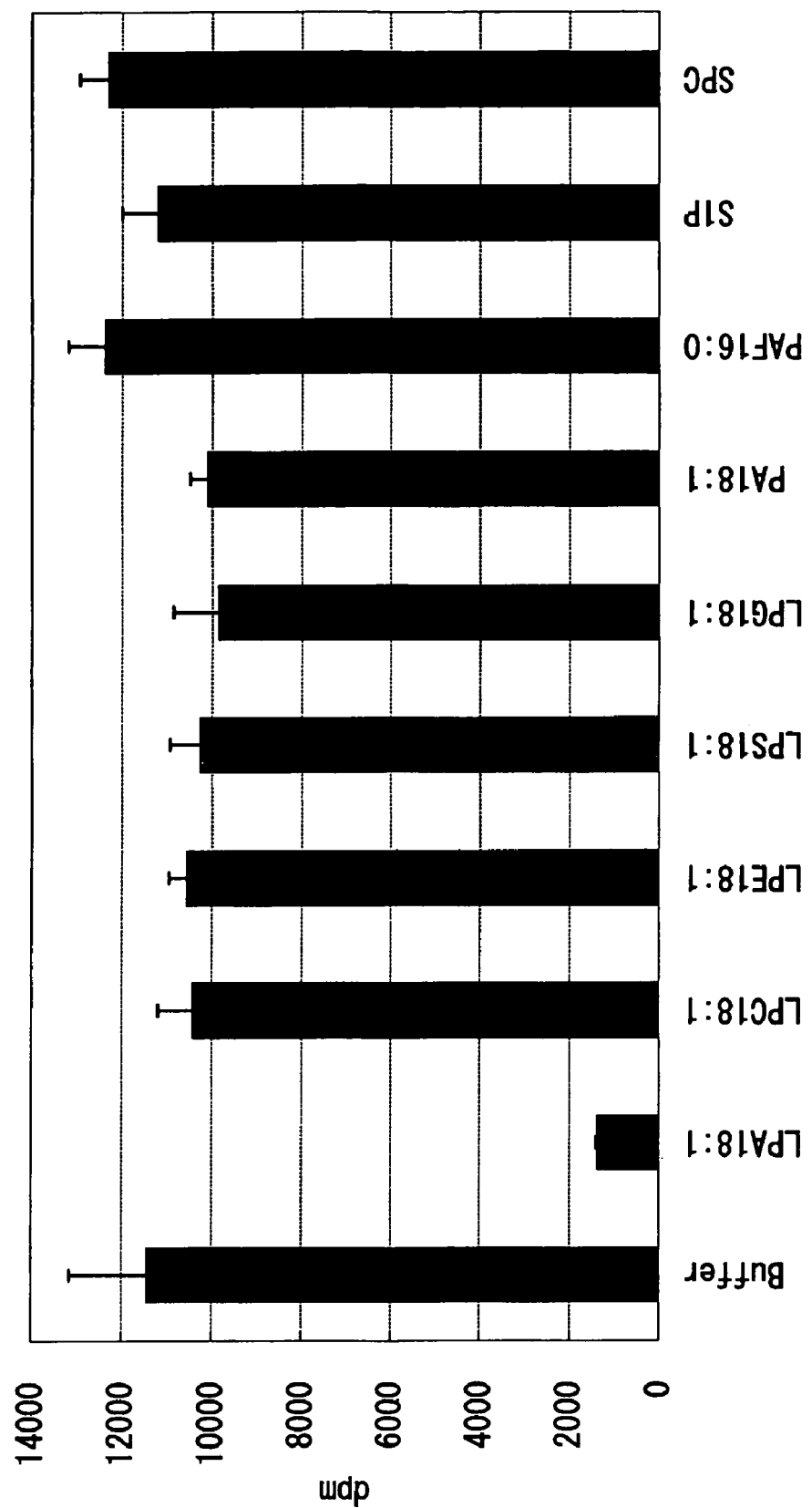
FIG. 25 shows the result of reactivity with other lipids than LPA, using the cell derived membrane fractions transiently expressing p2y9 receptors obtained from RH7777 cell. The buffer is a control to show total binding volume, where only tritium labeled LPA was used. The horizontal axis in FIG. 25 shows the detected radiation (dpm), whereas the vertical axis shows added lipids respectively.

The result was shown in FIG. 25. The vertical axis shows the detected radiation (dpm), whereas the horizontal axis in FIG. 25 shows the added lipids.

If the lipids added with LPA have affinity with p2y9, the considerable volume of added lipids may competitively bind to p2y9, resulting to inhibit the biding of labeled LPA to p2y9, and consequently the binding of labeled LPA is to be reduced. However, as shown in FIG. 25, the binding of labeled LPA to p2y9 has not been reduced by the addition of other lipids, it was thus revealed that all the monitored lipids did not exhibit higher affinity with p2y9 than LPA. That is to say, p2y9 binds more specifically to LPA than the other lipids.

Following to the above, kinetic analysis for binding ability of LPA to p2y9 has been performed, using RH7777 cell-derived membrane fractions transiently expressing p2y9 receptors.

RH7777 cell-derived membrane fractions were mixed with various concentrations of tritium labeled LPAs, reacted at 4° C. for 60 minutes, and thereby the total bindings were determined. In parallel to this, membrane fractions were also reacted with tritium labeled LPA in the same manner in the reaction mixture containing 10 µM of unlabeled LPA in order to determine the nonspecific bindings. The reaction mixture was filtrated by GF/C glass filter. The radioactivity still remained on the glass filter was determined as the volume of tritium labeled LPA binding with receptors. The specific binding value was calculated by subtracting the nonspecific binding value from the total binding value. As a negative control, the cells were transfected with pCXN2.1 vector instead of DNA encoding receptors, were used.

Figure 26:
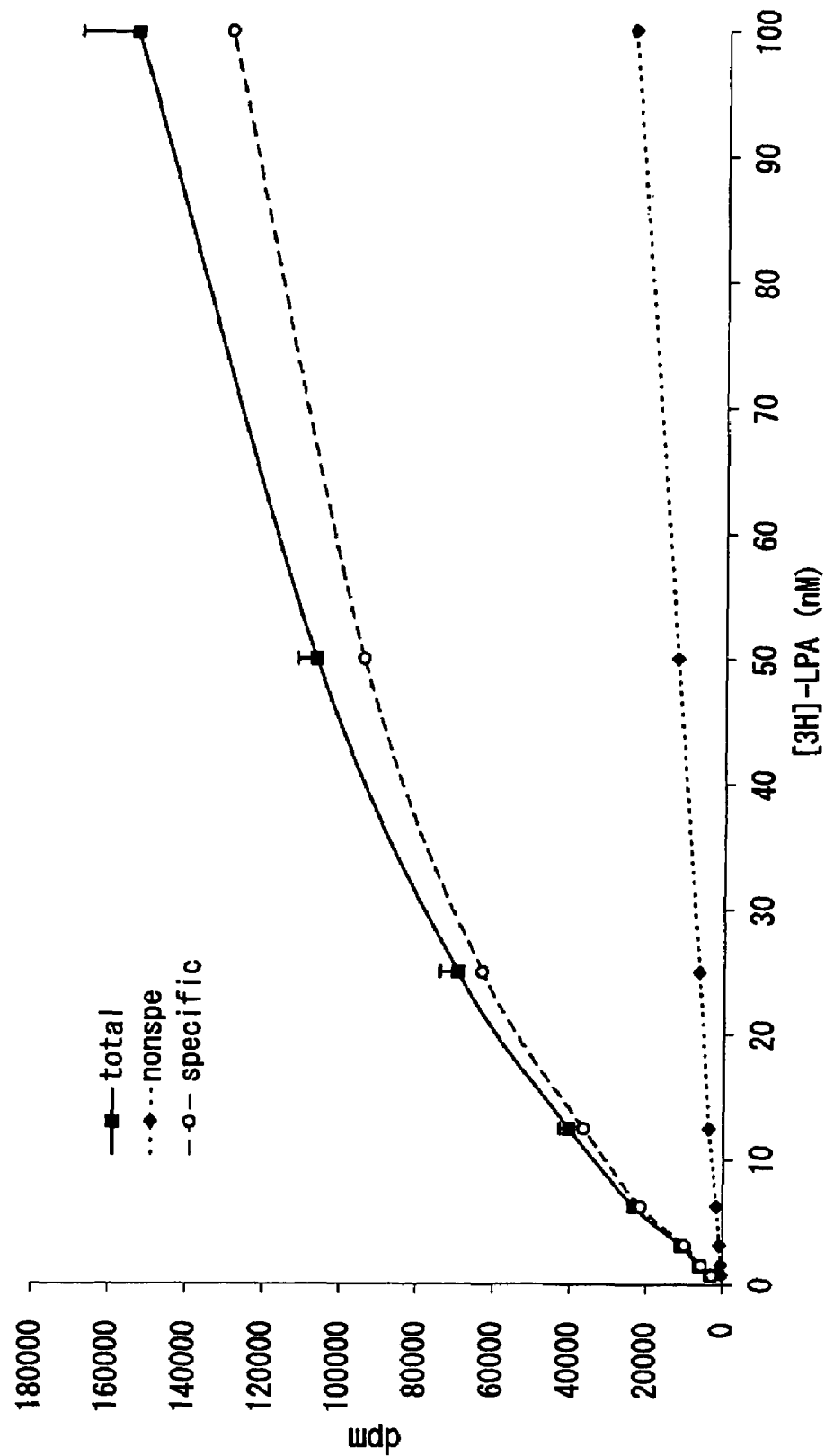
FIG. 26 shows the result of kinetic analysis for the binding characteristics of LPA to p2y9, using the cell derived membrane fractions transiently expressing p2y9 receptors obtained from RH-17777 cell transfected with p2y9 of the present invention.
Figure 27:
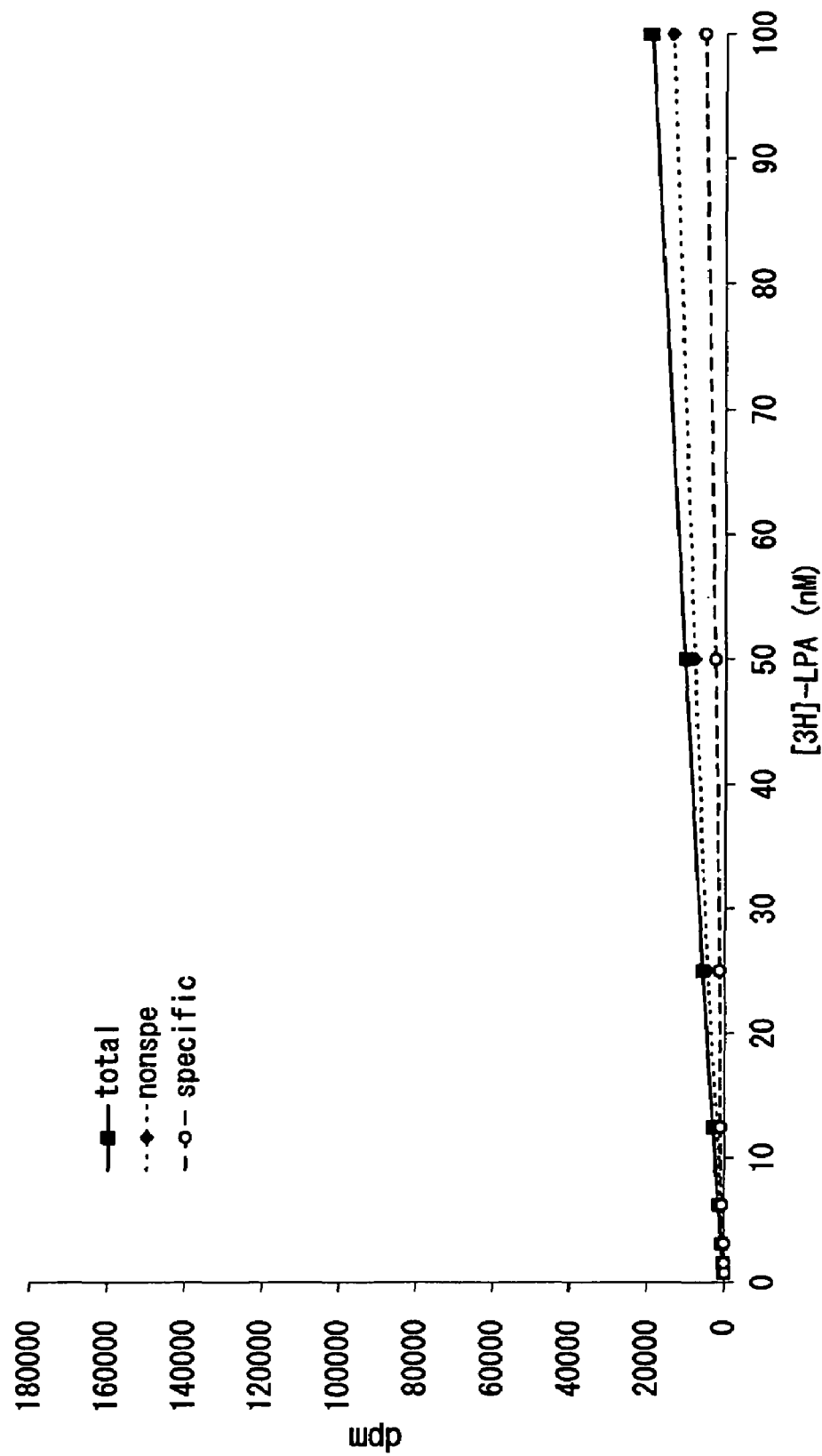
FIG. 27, the same as FIG. 26, the result of kinetic analysis for the binding characteristics of LPA to p2y9, using the cell derived membrane fractions transiently expressing p2y receptors obtained from RH7777 cell transfected with p2y9 of the present invention.

The results are shown in FIGS. 26 and 27. FIG. 26 shows the result when p2y9-transfected cell membranes were used. FIG. 27 shows the result of a negative control. The horizontal axis in each graph shows the concentration of tritium labeled LPA (nM), whereas the vertical axis shows the detected radiation (dpm). The closed square (■) represents the total bindings, closed diamond (▲) represents the nonspecific bindings and open circle (○) represents the specific bindings obtained by subtracting the nonspecific bindings from the total bindings.

Figure 28:
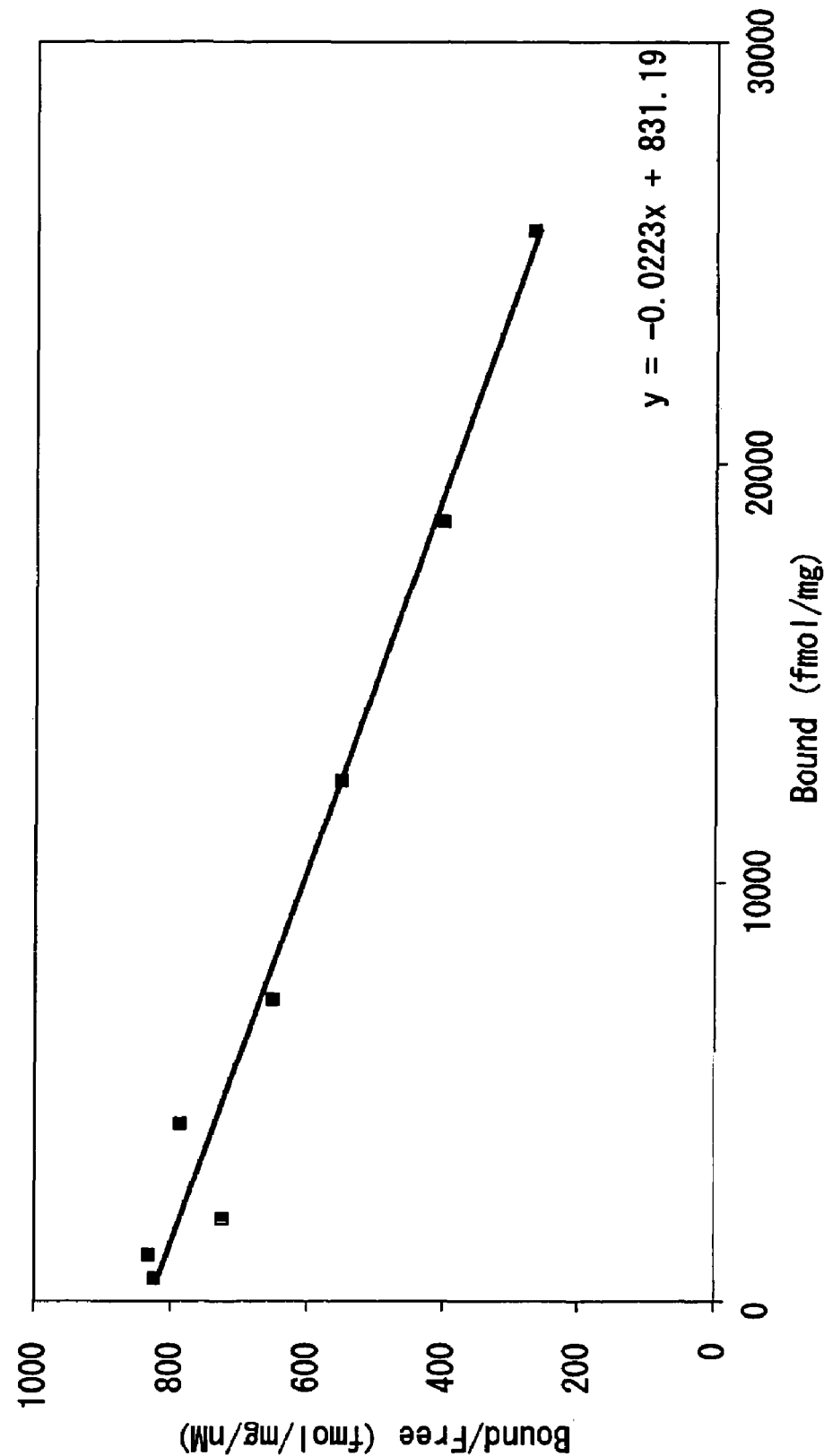
FIG. 28 is a graph to obtain kinetic parameters based on the results shown in FIGS. 26 and 27. The horizontal axis in FIG. 28 shows the bindings (f mol/mg), whereas the vertical axis shows binding/dissociation ratio (f mol/mg/nM).

FIG. 28 shows the graph to determine kinetic parameter based on the above findings. Specific Radioactivity of tritium-labeled LPA was 2109 GBq/mmol (57 Ci/mmol). The horizontal axis of FIG. 28 shows the binding capacity (fmol/mg), whereas the vertical axis shows binding/dissociation ratios (fmol/mg/nM). The resultant straight line is represented by the following equation: $Y=-0.0223x+831.19$ And consequentially yielded a $K_d$ value of 44.8 nM and $B_{max}$ value of 37.3 pmol/mg protein.

Further investigations have been carried out with respect to the functions of p2p9s by using PC-12 cells.

PC-12 cells were co-transfected with three types of DNA as shown below:
1. DNA encoding HA tagged-p2y9 introduced into pCxn2.1 vector
2. Firefly luciferase DNA of which expression is regulated by the rat zif promoter. zif-promoters can be activated correspondingly to the extracellular stimuli.
3. Renilla luciferase DNA of which expression is regulated by herpes simplex virus-thymidine kinase promoter. Thymidine kinase promoter exhibits constant activity independent of external stimuli.

The values of Firefly luciferase activity and Renilla luciferase activity were determined by stimulating the obtained transfectants with various concentrations of LPAs for 6 hours, and whereby calculated the value of Firefly luciferase activity versus Renilla luciferase activity. As a negative control, the cells transfected with pCXN2.1 vector instead of DNA encoding p2y9 were used.

Figure 29:
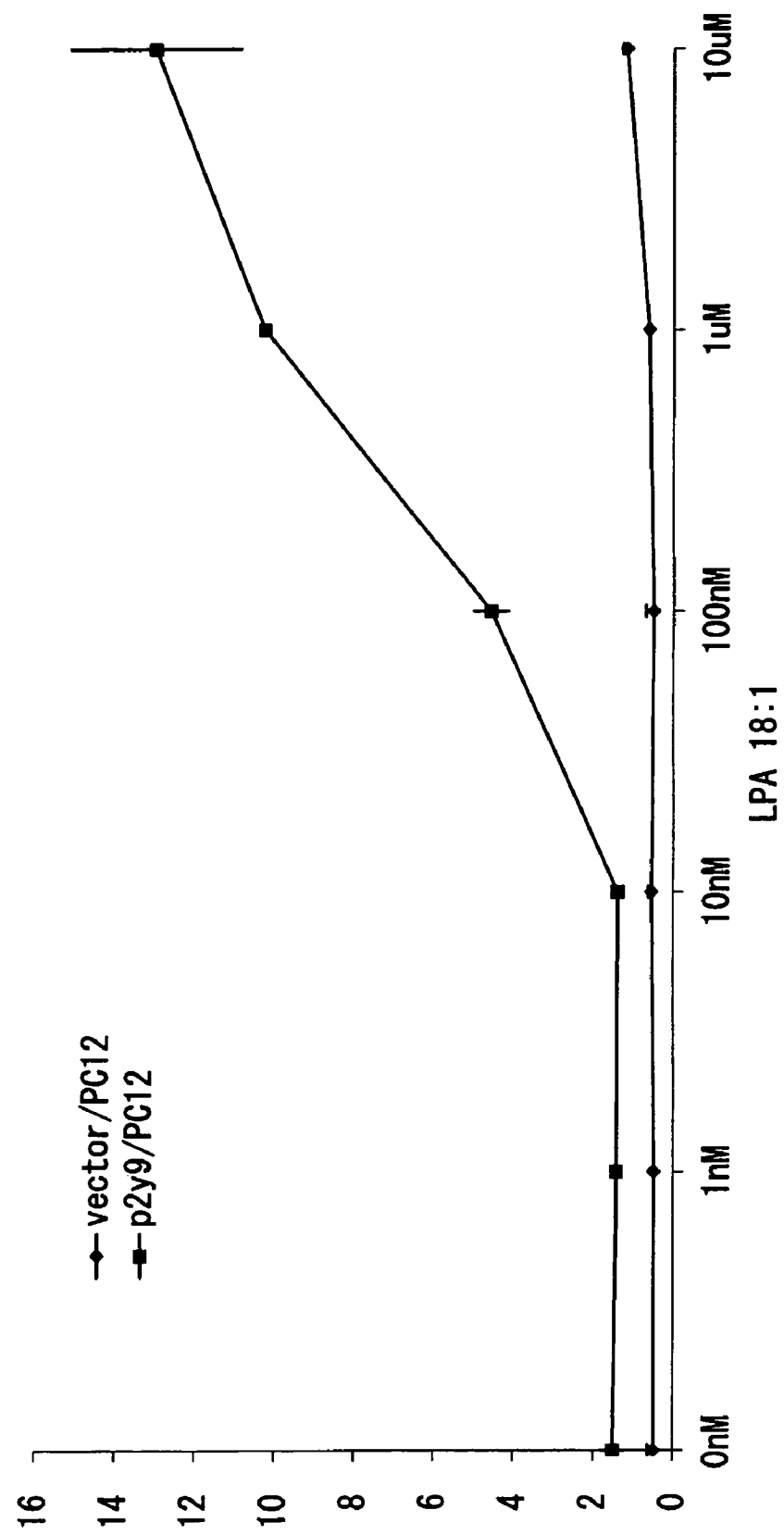
FIG. 29 shows the results of Luciferase Assay whereby evaluated the functions of p2y9 using PC-12 cells. The horizontal axis in FIG. 29 shows the concentration of LPA (nM to µM), whereas the vertical axis shows the ratios. The closed square (■) represents PC-12 cell transfected with p2y9, whereas the closed diamond (♦) represents negative control.

The results are shown in FIG. 29. The horizontal axis in FIG. 29 shows the concentration of LPA (nM to µM), whereas the vertical axis shows the ratios. The closed square (■) represents PC-12 cells transfected with p2y9 and the closed diamond (♦) represents a negative control.

zif promoters or tymidine kinase promoters, being the pormotors which can be activated according to the increase of cAMP or calcium concentrations, it is confirmed that p2y9 exhibits reactivity with LPA in a concentration dependent manner also in PC-12 cells. This finding also revealed that LPA receptors are not present endogenously in PC-12 cell at all or, if present, they may be fairly hyposensitive.

Figure 1:
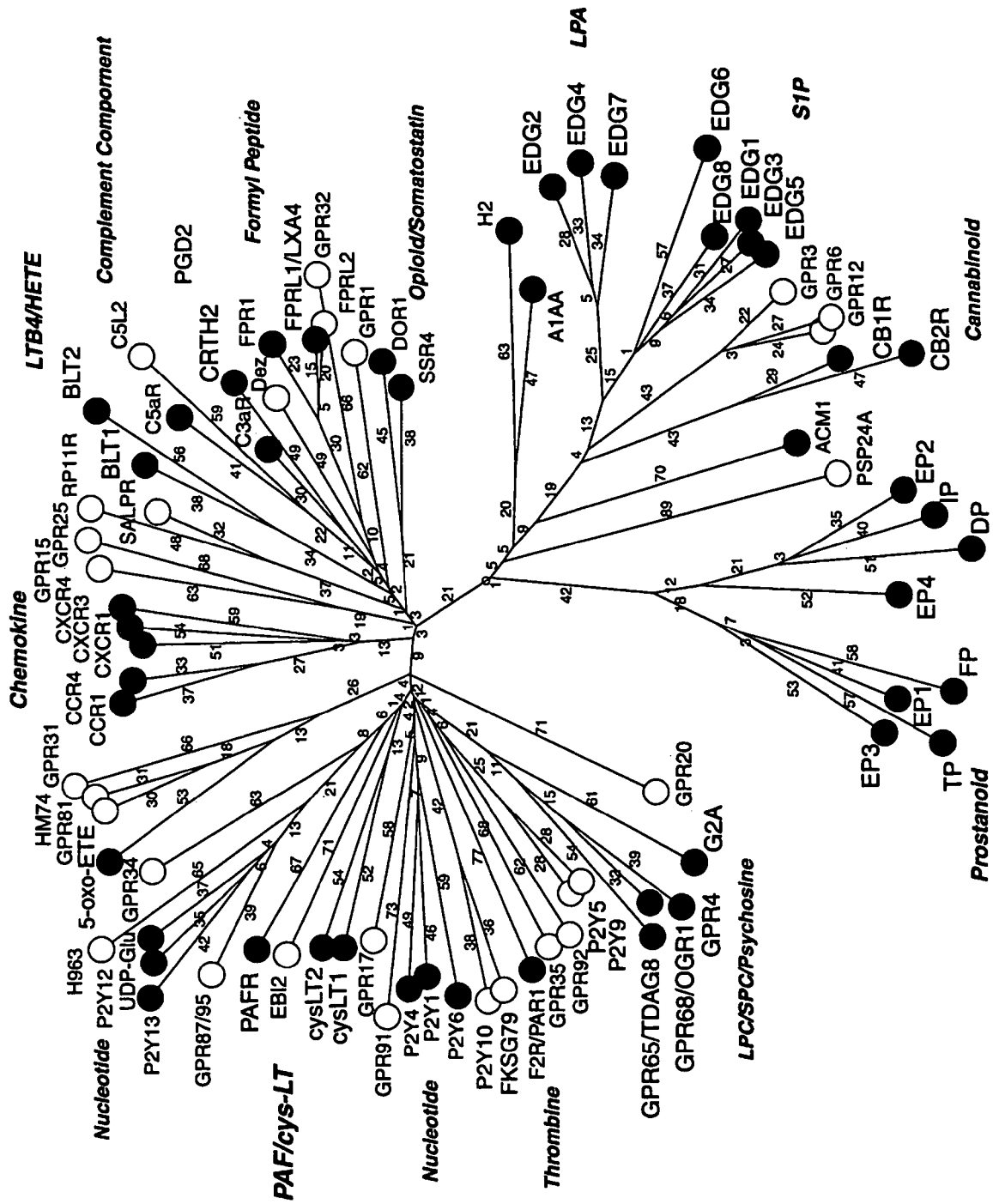
FIG. 1 shows the phylogenetic tree constructed for GPCR. The shorter sum of branch length between the two receptors indicates the more proximity between them.

As described above, p2y9 has been recognized as a receptor of LPA. p2y9, apparent from the phylogenetic tree in FIG. 1, shares no homology with EDG family or PSP24 which have been known as LPA receptors. Therefore, it can be recognized that the present invention is to provide a new and throughly different type of LPA receptor. The knowledge from the present invention that p2y9, conventionally sharing homology with PAF receptor, plays a role for a receptor of LPA, which is different from that of PAF's, contributes to Phylogenetic tree for GPCR by introducing a new approach.

The present invention is to provide a novel function of p2y9 that p2y9 is a receptor of LPA, and the use thereof.

p2y9 of the present invention can be any, including those of human and mouse, as far as it has the function of p2y9. p2y9, preferably has an amino acid sequence represented by the SEQ ID NO:1, but not limited to the whole sequence thereof. The sequence wherein one or more amino acids may be deleted, substituted, or added, or may have any combination thereof as far as it has the function of p2y9.

The LPA of the present invention is not limited to 1-oleoyl-LPA used for the above test experiment, but may be the LPA, wherein the hydroxyl group at the 3-position of glycerin is bonded with phosphate group, and the hydroxyl group of at the 1- or 2-position is bonded optionally with acyl group, alkenyl group or alkyl group, or may be the derivative thereof, as far as it has reactivity with p2y9.

According to the present invention, LPA, wherein hydroxyl group is bonded with acyl group at the 1-position of glycerin is called 1-acyl-LPA. LPA, wherein hydroxyl group is bonded with acyl group at the 2-position of glycerin is called 2-acyl-LPA. In the same manner as the above, LPA, wherein hydroxyl group is bonded with alkenyl group is called 1-alkenyl-LPA or 2-alkenyl-LPA, and wherein hydroxyl group is bonded with alkyl group is called 1-alkyl-LPA or 2-alkyl-LPA. Acyl groups bonding to glycerin are preferably acyl groups derived from saturated or unsaturated fatty acids, typically including acyl groups derived from such as palmitic acid, stearic acid, linoleic acid, oleic acid and arachidonic acid. Alkenyl groups, for example, include those having a straight or branched chain containing 10 to 30, preferably 14 to 22 carbon atoms, preferably having a straight chain, wherein the said alkenyl groups optionally have one or more, preferably one unsaturated bond. Examples of alkenyl groups include such as 1-hexadecenyl group and 1-octadecenyl group. Alkyl groups, for example, include those having a straight or branched chain containing 10 to 30, preferably 14 to 22 carbon atoms, preferably having a straight chain. Examples of alkyl group include such as a hexadecyl group and an octadecyl group.

p2y9 being a receptor of LPA, p2y9 of the present invention can be used to screen various physiological activities stimulated or inhibited by LPA. The method of screening of the present invention can be performed by letting p2y9 expressed in the cell, or using the cell or membrane already having p2y9 therein. The screening method of the present invention are not limited to any particular ones as described above, but include the methods to screen the substances having activities with LPA by using p2y9 as a receptor of LPA.

Meanwhile, all the contents disclosed in the specification of Japanese Patent Application No. 2003-007657 will be incorporated herein.

EXAMPLES

The present invention will now be more specifically illustrated by way of the following Examples although the present invention is not limited by those Examples.

Example 1

Introducing Receptors to CHO Cells

DNAs encoding four types of orphan receptors such as GPR34, p2y5, p2y9 and p2y10 tagged with HA comprising 9 amino acids residue at N terminus were respectively introduced into pCXN2.1 vectors (see FIG. 2) and consecutively transfected into CHO cells using Lipofectamine PLUS reagent (Invitrogen). Cells were incubated in Ham's F-12 supplemented with 10% fetal bovine serum. After proliferation of clones derived from a single cell from the CHO cell line in the presence of 2 g/L neomycin, plurality of clones stably expressing HA-tags on the cell surface were selected by flow cytometric analysis and thereby obtained clones stably expressing individual receptors.

Example 2

Determination of Lipid Induced Calcium Concentration Changes in Individual Clones CHO clones of four individual receptors such as GPR34, p2y5, p2y9 and p2y10 were seeded respectively in three 96-well plates at a density of $4 \times 10^4$ cells/well. On the following day, cells were loaded with 4 μM of Fluo-3 (calcium indicator) and incubated at 37° C. for 1 hour for incorporation of Fluo-3. Cells were then reacted with individual lipids (1 to 10 μM) contained in the Lipid Library of BIOMOL comprising over 200 kinds of lipid molecules and 17 nucleotides (1 to 100 μM) such as ATP, then time course kinetics of intracellular calcium mobilization was monitored with FLEXstation of Molecular Devices.

CHO cells endogenously expressing ATP receptors, the remarkable change in intracellular calcium concentration beyond the measurable range has been detected in ATP added clones. This enabled to confirm the relevance of the experiment.

On the other hand, unlikely to the case of ATP, the intracellular calcium increase, not in entire clones but, specific to the expressed receptors was recognized when p2y9-expressing clones was reacted with LPA.

Example 3

Determination of LPA-Dependent Calcium Concentration Changes in Individual Clones CHO clones stably expressing four types of receptors such as GPR34, p2y5, p2y9 and p2y10 respectively were used to monitor the intracellular calcium concentration change in each cell in the same manner as described in Example 2.

The result was shown in FIG. 3.

Example 4

Determination of the Changes in cAMP Concentration in Each Clone

CHO clones stably expressing four types of receptors such as GPR34, p2y5, p2y9 and p2y10 respectively were suspended in HBSS containing 5 mM HEPES-NaOH (pH 7.4), 0.1% BSA and 500 μM IBMX (inhibitor of cAMP degradation enzyme). The cells at the density of $1 \times 10^5$ cells/well were seeded in 384-well plates, and reacted with 59 lipids selected from the Lipid Library of BIOMOL or 17 nucleotides under coexistence of 50 μM forskolin (receptor-independent adenylate cyclase activator) at room temperature for 30 minutes. The intracellular cyclic AMP (cAMP) concentration was then measured using an AlphaScreen cAMP assay kit (Packard).

The results were shown in FIGS. 4 to 10.

When CHO cells expressing p2y9 were reacted with LPA, a significant increase in cAMP concentration has been observed (see FIG. 8).

Example 5

Comparison of p2y9 Clones

Four types of CHO clones, #01, #09, #15 and #20, stably expressing p2y9 were incubated for 24 hours in the medium of Ham's F-12 supplemented with 0.1% BSA in replacement of Ham's F-12 supplemented with 10% fetal bovine serum. The cells were then suspended in HEPES-Tyrode's buffer (140 mM NaCl, 2.7 mM KCl, 1 mM $CaCl_2$, 12 mM $NaHCO_3$, 5.6 mM D-glucose, 0.49 mM $MgCl_2$, 0.37 mM $NaH_2PO_4$, and 25 mM HEPES-NaOH (pH 7.4)) containing 3 μM Fura-2 (calcium indicator) and 0.01% Cremophor EL. Cells were incubated at 37° C. for 1 hour for incorporation of Fura-2. Cells were then resuspended in HEPES-Tyrode's buffer in order to achieve a cell density of $1\times10^6$ cells/ml. The changes in intracellular concentrations with addition of various concentrations of LPAs were monitored by using CAF-100 spectrofluorometer (Jasco, Tokyo, Japan). As a negative control, CHO cells which acquired neomycin resistance by transfected only with pCXN2.1 vector were used.

The results were shown in FIGS. 11 to 14 respectively.

Example 6

Reactivity of Individual p2y9 Clones with Thrombin, Etc.)

Instead of LPA, thrombin (0.1 NIH units/ml), PAF (1 μM) and ATP (10 μM) were added to four individual CHO clones, #01, #09, #15 and #20, stably expressing p2y9, wherein increase in intracellular calcium concentrations were measured in the same manner as described in Example 5.

The result is shown in FIG. 15. There were no significant difference exhibited in thrombin, PAF and ATP relative to the negative control.

Example 7

Comparison Between p2y9 Clone and p2y5 Clone

Each CHO clone stably expressing p2y9 or p2y5 incubated for 24 hours in Ham's F-12 medium supplemented with 0.1% BSA instead of 10% fetal bovine serum, was suspended in HBSS containing 5 mM HEPES-NaOH (pH 7.4), 0.1% BSA and 500 μM IBMX. The cells treated with 5 μM forskolin were seeded in 384-well plates at the density of $1\times10^5$ cells/well. Or the cells without forskolin treatment were seeded in 384-well plates at a density of $1\times10^6$ cells/well. Cells are then treated with various concentrations of LPAs at room temperature for 30 minutes and the concentration of intracellular cAMP was measured using an AlphaScreen cAMP assay kit (Packard). As a negative control, CHO cells which acquired neomycin resistance by transfected only with pCXN2.1 vector were used.

The results were shown in FIGS. 16 to 17.

Example 8

The Expression of p2y9 and p2y5 in RH7777 Cell or B103 Cell, and the Reactivity Thereof with LPA RH7777 Cells or B103 cells were transfected with pCXN2.1 vector wherein DNA encoding HA-tagged p2y9 or p2y5 were introduced, using LipofectAMINE 2000 reagent (Invitrogen). After 24 hours of incubation in DMEM supplemented with 10% fetal bovine serum, cells were incubated for another 24 hours in the replaced medium of DMEM supplemented with 0.1% BSA. Cells were scraped off, suspended in binding buffer (25 mM HEPES-NaOH (pH 7.4), 10 mM $MgCl_2$, 0.25 M sucrose), sonicated with metal probe and centrifuged at 800×g. The supernatant was further ultra-centrifuged at $10^5\times g$ to yield the precipitate. The obtained precipitate was resuspended in the binding buffer to yield the cell-derived membrane fractions transiently expressing the receptors.

In order to determine the quantitative total bindings with respect to each concentration of LPA, the membrane fractions containing 50 μg of protein were mixed with 1 nM, 3 nM and 10 nM of Tritium labeled LPAs respectively in the binding buffer containing 0.25% BSA (final volume of 200 μl) and reacted at 4° C. for 60 minutes. In parallel to this, in order to determine the nonspecific bindings in respective concentrations, membrane fractions were also reacted with tritium labeled LPAs in the same manner in the reaction mixture containing a 500-fold concentration of unlabeled LPA.

The reaction mixture was filtrated by GF/C glass filter (Packard). The filter was then washed with binding buffer containing 0.25% BSA. The radioactivity still remained on the glass filter after washing was determined as the volume of tritium labeled LPA binding with receptors. The specific binding value was calculated by subtracting the nonspecific binding value from the total binding value. As a negative control, the cells were transfected with pCXN2.1 vector instead of DNA encoding receptors.

The results with RH7777 cells are shown in FIGS. 19 to 21, whereas the results with B103 cells are shown in FIGS. 22 to 24.

Example 9

RH7777 Cells were transfected with pCXN2.1 vector wherein DNA encoding HA-tagged p2y9 or p2y5 were introduced, using LipofectAMINE 2000 reagent (Invitrogen). After 24 hours of incubation in DMEM supplemented with 10% fetal bovine serum, cells were incubated for another 24 hours in the replaced medium of DMEM supplemented with 0.1% BSA. Cells were scraped off, suspended in binding buffer (25 mM HEPES-NaOH (pH 7.4), 10 mM $MgCl_2$, 0.25 M sucrose), sonicated with metal probe and centrifuged at 800×g. The supernatant was further ultra-centrifuged at $10^5\times g$ to yield the precipitate. The resultant precipitate was resuspended in the binding buffer to yield the cell-derived membrane fraction transiently expressing the receptors.

In order to obtain the total bindings of LPA, the membrane fractions containing 20 μg of protein were mixed with 5 nM of Tritium labeled LPA in the binding buffer containing 0.25% BSA (final volume of 200 μl) and reacted at 4° C. for 60 minutes. (the result is shown in FIG. 25 as buffer). In parallel to this, membrane fractions were reacted with tritium labeled LPA in the same manner in the reaction mixture containing 5 nM of Tritium labeled LPA and 1 μM of unlabeled LPAs (LPC: lysophosphatidylcholine, LPE: lysophosphatidylethanolamine, LPS: lysophosphatidylserine, LPG; lysophosphatidylglycerol, PA: phosphatidyic acid, PAF: platelet activating factor, S1P: sphingosine-1-phosphate, SPC: sphyngosylphosphocholine).

The reaction mixture was filtrated by GF/C glass filter (Packard). The filter was then washed with binding buffer containing 0.25% BSA. The radioactivity still remained on the glass filter after washing was determined as the volume of tritium labeled LPA binding with receptors.

The results are shown in FIG. 25. If the added lipids have affinity with p2y9, they were supposed to binds to p2y9 competitively with LPAs, resulting to inhibit the binding of LPAs to p2y9 resulting to the decrease in the tritium labeled LPA bindings. However as shown in FIG. 25, the examined lipids other than LPAs did not show as high affinity with p2y9 as LPAs do.

Example 10

Kinetic Analysis of LPA Binding to p2y9

RH7777 Cells were transfected with DNA encoding HA-tagged p2y9 introduced into pCXN2.1 vector, using LipofectAMINE 2000 reagent (Invitrogen). After 24 hours of incubation in DMEM supplemented with 10% fetal bovine serum, cells were incubated for another 24 hours in the replaced medium of DMEM supplemented with 0.1% BSA. Cells were scraped off, suspended in binding buffer (25 mM HEPES-NaOH (pH 7.4), 10 mM $MgCl_2$, 0.25 M sucrose), sonicated with metal probe and centrifuged at 800×g. The supernatant was further ultra-centrifuged at $10^5$×g to yield the precipitate. The resultant precipitate was resuspended in the binding buffer to yield the cell-derived membrane fraction transiently expressing the receptors.

In order to obtain the total bindings of LPA in various concetrations, the membrane fractions containing 40 μg of protein were mixed with various concentrations of Tritium labeled LPAs respectively in the binding buffer containing 0.25% BSA (final volume of 200 μl) and reacted for at 4° C. 60 minutes. In parallel to this, in order to obtain the total of nonspecific bindings with various concentrations of LPAs, membrane fractions were reacted with tritium labeled LPA in the same manner in the reaction mixture containing 10 μM of unlabeled LPA.

The reaction mixture was filtrated by GF/C glass filter (Packard). The filter was then washed with binding buffer containing 0.25% BSA. The radioactivity still remained on the glass filter after washing was determined as the volume of tritium labeled LPA binding with receptors. The specific binding value was calculated by subtracting the nonspecific binding value from the total binding value. As a negative control, the cells were transfected with pCXN2.1 vector instead of DNA encoding receptors.

The results are shown in FIGS. 26 and 27 respectively. The graph of the comprehensive analysis with respect to the binding of LPA to p2y9 is shown in FIG. 28. Specific Radioactivity of tritium-labeled LPA was 2109 GBq/mmol (57 Ci/mmol). As shown in FIG. 28, the resultant values are fitted approximately on a straight line, which is represented by the following equation: y=−0.0223 x+831.19

And consequentially yielded a $K_d$ value of 44.8 nM and $B_{max}$ value of 37.3 pmol/mg protein.

Example 11

Luciferase Analysis with PC-12 Cell

In the DMEM medium supplemented with 0.5% horse serum and 0.25% fetal bovine serum, in replacement of DMEM supplemented with 10% horse serum and 5% fetal bovine serum, PC-12 cells were co-transfected with three types of DNA as shown below:
1. DNA encoding HA tagged-p2y9 introduced into pCxn2.1 vector
2. Firefly luciferase DNA of which expression is regulated by the rat zif promoter.
3. Renilla luciferase DNA of which expression is regulated by herpes simplex virus-thymidine kinase promoter.

SuperFect (Qiagen) was used as a transfection reagent. Cells at a density of 2×$10^5$ cells/well were seeded in 24-well plates and incubated for 12 hours. The medium was then replaced to DMEM supplemented with 0.1% BSA, where cells were then incubated for another 24 hours.

The values of Firefly and Renilla luciferase activities after 6 hours of stimulation of the cells with various concentrations of LPAs, were measured using PICAGENE Dual Seapansy Kit (Toyo Ink) and LB 9506 luminometer (Berthold) and whereby calculated the value of firefly luciferase activity versus renilla luciferase activity. As a negative control, the cells are transfected with pCXN2.1 vector instead of DNA encoding p2y9.

The result was shown in FIG. 29.

INDUSTRIAL APPLICABILITY

Lysophosphatidic acid: LPA, same as a platelet activating factor (PAF) and sphingosine-1-phosphate (S1P), has come to be recognized as one of "lysophospholipid mediators". LPA has come to be known to play a various roles in diverse tissues such as cell proliferation, retraction of neurite which is essential to the maturation of neuron, induction of carcinoma cell invasion, smooth muscle contraction, platelet aggregation, suppression of cell apoptosis and promotion of cellular chemotaxis. However, the functional mechanism or the receptor thereof has not yet been revealed. The explicit identification of the functional mechanism of LPA receptor in vivo is indispensable for the recovery from various disorders resulting from LPA associated physiological activities, therefore the characterization of functional mechanism of LPA has been highly demanded.

The present invention is to elucidate a new type of receptors for LPA, and by having done so, it is also to provide a potent screening method for the development of new pharmaceutical and diagnostic preparations for a wide range of LPA associated physiological activities. p2y9, characterized as LPA receptor by the present invention, sharing fairly little amino acids sequence homology with EDG family or PSP24 known as LPA receptors, is to provide a new field in the art which contributes to reveal a wide range of physiological activities in LPA.

The invention claimed is:

1. A method of screening for a candidate compound that acts as an agonist of a G protein-coupled receptor p2y9, comprising:
   (a) preparing a first group and a second group of cells that express the G protein-coupled receptor p2y9 on the cell surfaces;
   (b) adding LPA to the cell surfaces of the first group of cells;
   (c) monitoring an intracellular activity in the first group of cells, said intracellular activity being associated with binding of LPA to p2y9;
   (d) adding said candidate compound to the second group of cells;
   (e) monitoring an intracellular activity in the second group of cells, said intracellular activity being the same as the intracellular activity of step (c);
   (f) comparing the intracellular activity in step (c) with the intracellular activity in step (e); and
   (g) determining whether said candidate compound is an agonist of the G protein-coupled receptor p2y9 based on the comparison in step (f),
   wherein said G protein-coupled receptor p2y9 comprises seven transmembrane regions, and
   wherein said G protein-coupled receptor p2y9 comprises an amino acid sequence represented by SEQ ID NO: 1.

2. The method according to claim 1, wherein the monitoring the intracellular activity in steps (c) and (e) comprises detecting calcium concentration in the cells.

3. The method according to claim 1, wherein the monitoring the intracellular activity in steps (c) and (e) comprises detecting cAMP concentration in the cells.

4. A method of screening for a candidate compound that acts as an antagonist of a G protein-coupled receptor p2y9, comprising:
   (a) preparing a first group and a second group of cells that express the G protein-coupled receptor p2y9 on the cell surfaces;
   (b) adding LPA to the cell surfaces of the first group of cells;
   (c) monitoring an intracellular activity in the first group of cells, said intracellular activity being associated with binding of LPA to p2y9;
   (d) adding said candidate compound and LPA to the second group of cells;
   (e) monitoring an intracellular activity in the second group of cells, said intracellular activity being the same as the intracellular activity of step (c);
   (f) comparing the intracellular activity in step (c) with the intracellular activity in step (e); and
   (g) determining whether said candidate compound is an antagonist of the G protein-coupled receptor p2y9 based on the comparison in step (f),
   wherein said G protein-coupled receptor p2y9 comprises seven transmembrane regions. and
   wherein said G protein-coupled receptor p2y9 comprises an amino acid sequence represented by SEQ ID NO: 1.

5. The method according to claim 4, wherein the monitoring the intracellular activity in steps (c) and (e) comprises detecting calcium concentration in the cells.

6. The method according to claim 4, wherein the monitoring the intracellular activity in steps (c) and (e) comprises detecting cAMP concentration in the cells.

7. The method according to claim 4, wherein the candidate compound is an inhibitor of carcinoma cell invasion.

8. A method of screening for a candidate compound that acts as an inhibitor of binding of LPA to G protein-coupled receptor p2y9, comprising:
   (a) preparing a plurality of groups of cells that express the G protein-coupled receptor p2y9 on the cell surfaces;
   (b) adding (1) the candidate compound and (2) labeled LPA to each of said plurality of groups of cells that express the G protein-coupled receptor p2y9 on the cell surfaces, said candidate compound being added in a different concentration to each of said plurality of groups of cells that express the G protein-coupled receptor p2y9 on the cell surfaces,
   (c) detecting activity of said labeled LPA bound to the G protein-coupled receptor p2y9 in each of said plurality of groups of cells that express the G protein-coupled receptor p2y9 on the cell surfaces, and
   (d) determining that said candidate compound is an inhibitor of binding of LPA to G protein-coupled receptor p2y9 when the activity detected in step (c) decreases dose-dependently with the candidate compound among said plurality of groups of cells that express the G protein-coupled receptor p2y9 on the cell surfaces,
   wherein said G protein-coupled receptor p2y9 comprises seven transmembrane regions, and
   wherein said G protein-coupled receptor p2y9 comprises an amino acid sequence represented by SEQ ID NO: 1.

9. The method according to claim 8, wherein said inhibitor of binding of LPA to G protein-coupled receptor p2y9 is an agonist candidate of G protein-coupled receptor p2y9.

10. The method according to claim 8, wherein said inhibitor of binding of LPA to G protein-coupled receptor p2y9 is an antagonist candidate of G protein-coupled receptor p2y9.

* * * * *